(12) United States Patent
Kanamori et al.

(10) Patent No.: US 9,365,876 B2
(45) Date of Patent: Jun. 14, 2016

(54) METHOD FOR PRODUCING CHEMICAL BY CONTINUOUS FERMENTATION

(75) Inventors: Satoko Kanamori, Otsu (JP); Jihoon Cheon, Otsu (JP); Takashi Mimitsuka, Kamakura (JP); Norihiro Takeuchi, Otsu (JP); Makoto Nishida, Otsu (JP); Yuji Tanaka, Otsu (JP)

(73) Assignee: Toray Industries, Inc. (JP)

( * ) Notice: Subject to any disclaimer, the term of this patent is extended or adjusted under 35 U.S.C. 154(b) by 205 days.

(21) Appl. No.: 13/992,443

(22) PCT Filed: Dec. 8, 2011

(86) PCT No.: PCT/JP2011/078392
§ 371 (c)(1),
(2), (4) Date: Aug. 7, 2013

(87) PCT Pub. No.: WO2012/077742
PCT Pub. Date: Jun. 14, 2012

(65) Prior Publication Data
US 2013/0330787 A1    Dec. 12, 2013

(30) Foreign Application Priority Data
Dec. 9, 2010 (JP) ................................ 2010-274324

(51) Int. Cl.
| | | |
|---|---|---|
| *C12P 1/00* | (2006.01) | |
| *C12P 13/04* | (2006.01) | |
| *C12P 13/08* | (2006.01) | |
| *C12P 7/40* | (2006.01) | |
| *C12P 7/56* | (2006.01) | |
| *C12P 13/00* | (2006.01) | |
| *C12M 1/00* | (2006.01) | |
| *C12M 1/26* | (2006.01) | |
| *C12M 1/34* | (2006.01) | |

(52) U.S. Cl.
CPC ............... *C12P 13/08* (2013.01); *C12M 29/02* (2013.01); *C12M 29/18* (2013.01); *C12M 33/14* (2013.01); *C12M 41/40* (2013.01); *C12M 47/10* (2013.01); *C12P 7/40* (2013.01); *C12P 7/56* (2013.01); *C12P 13/001* (2013.01); *C12P 13/04* (2013.01)

(58) Field of Classification Search
CPC ............. C12P 1/00; C12P 13/00; C12P 13/04
See application file for complete search history.

(56) References Cited

U.S. PATENT DOCUMENTS

| | | | |
|---|---|---|---|
| 5,143,833 A | 9/1992 | Datta | |
| 5,770,435 A | 6/1998 | Donnelly et al. | |
| 2003/0153059 A1* | 8/2003 | Pilkington | .............. C12C 11/07 435/161 |
| 2009/0269812 A1* | 10/2009 | Sawai | ..................... C12P 13/04 435/88 |

FOREIGN PATENT DOCUMENTS

| | | |
|---|---|---|
| JP | 62-138184 | 6/1987 |
| JP | 10-174594 | 6/1989 |
| JP | 05-095778 | 4/1993 |
| JP | 6-345683 | 12/1994 |
| JP | 7-024264 | 1/1995 |
| JP | 11-057427 | 3/1999 |
| JP | 11-215980 | 8/1999 |
| JP | 2000-317273 | 11/2000 |
| JP | 2005-27533 | 2/2005 |
| JP | 2005-88008 | 4/2005 |
| JP | 3948593 | 7/2007 |
| JP | 2007-252367 | 10/2007 |
| JP | 2008-212138 | 9/2008 |
| JP | 2010-029108 | 2/2010 |
| WO | 2007/097260 | 8/2007 |

OTHER PUBLICATIONS

U.S. Appl. No. 14/388,306; U.S. Appl. No. 13/996,241.*
Chinese Office Action mailed Apr. 25, 2014 for Chinese Application No. 201180058917.1 along with English translation.
McKinlay, J. B. et al., "Insights into *Actinobacillus succinogenes* Fermentative Metabolism in a chemically defined Growth Medium," *Applied and Environmental Microbiology*, Nov. 2005, vol. 71, No. 11, pp. 6651-6656.
Tanaka, A. et al., "Shear Stress on a Membrane Exerted by the Flow with Random Fluctuation Due to Aeration," *The Japan Society of Mechanical Engineers*, Jul. 9, 2001, pp. 312-315.
Supplementary European Search Report mailed Nov. 19, 2014 from corresponding European Patent Application No. 11 84 7535.
Notification of Reasons for Refusal dated Dec. 22, 2015 of corresponding Japanese Application No. 2012-510058, along with an English translation.

* cited by examiner

*Primary Examiner* — Ruth Davis
(74) *Attorney, Agent, or Firm* — DLA Piper LLP (US)

(57) ABSTRACT

A method produces a chemical through continuous fermentation including: (a) culturing a cell in a culture medium in a fermentor to ferment a feedstock to produce a chemical; (b) conducting filtration of the culture medium with a separation membrane module; (c) separating a permeate containing the chemical from the culture medium while retaining a non-permeated liquid in the fermentor, and (d) supplying a gas from at least one of a lower portion of the separation membrane module and a pipe communicating between the fermentor and the separation membrane module to adjust a gas linear velocity in the separation membrane module to 0.15 cm/s to 70 cm/s while supplying the separation membrane module with a liquid.

13 Claims, 14 Drawing Sheets

```
                        SEQUENCE LISTING

<160> NUMBER OF SEQ ID NOS: 20

<210> SEQ ID NO 1
<211> LENGTH: 999
<212> TYPE: DNA
<213> ORGANISM: Xenopus laevis

<400> SEQUENCE: 1
atggcaactg tgaaggataa actcatccac aatgtggtca aggaggagtc gctcccccag      60
aacaaggtca ccattgtggg tgtgggggcc gtgggcatgg cctgtgccat cagtgtcctg     120
cagaaggatt tggcagatga gcttgcactt gttgatgtga tagaagacaa actgaagggg     180
gaaatgatgg atctccagca tggcagtctg ttccttcgta cccccaagat tgtctcaggg     240
aaagattaca gcgtcactgc aaactccaag ctggtagttg tgacggccgg ggcccgtcag     300
caggagggag agagtcgcct gaatctggtt cagcgcaatg tcaacatctt caaattcatc     360
attcccaaca ttgtcaagta cagccccaac tgcaccctgc tcatcgtctc caccccagtg     420
gacattctga catatgtggc ctggaagatc agtggattcc ccaaaaaccg tgtcattggc     480
agcggctgca atttggactc tgcccgtttc cgttacctca tggggcagaa gtttgggatc     540
cacacccaga gctgccacgg ttgggtcatt ggggaacacg gagactcgag tgtgccagtg     600
tggagtgggg tgaatgtggc tggcgtgtcc ctgaaaaccc tgcaccccga tattgggagt     660
gacgcagaca aggagaactg gaaggaggtg cacaagcagg ttgtggacag cgcctatgaa     720
gtgatcaagc tgaagggcta cacctcctgg gctattggcc tgtccgtagc tgacctgtct     780
gagagtatcc tgaagaacct ccgccgagtc catcccattt ccacaatggt caagggcatg     840
tacggcgtga ataatgatgt tttcctcagt gtccctgtg tgttgggcaa cttgggcatc      900
acagacgtgg ttaacatgac gctgaaggca gatgaagagg atcgcttacg caagagcgca     960
gacaccctgt gggccatcca gaaggagctg cagttctag                            999

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gtcgacatgg caactgtgaa ggataa                                            26

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcggccgcct agaactgcag ctcctt                                            26

<210> SEQ ID NO 4
<211> LENGTH: 85
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 4
tctcaattat tattttctac tcataacctc acgcaaaata acacagtcaa atcaatcaaa    60
atggcaactg tgaaggataa actca                                          85

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aggcgtatca cgaggccctt                                                20

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaattaattc ttgaagacga aagggcctcg tgatacgcct agattgtact gagagtgcac    60

<210> SEQ ID NO 7
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7 tattttcgt tacataaaaa tgcttataaa actttaacta ataattagag attaaatcgc     60
ctgtgcggta tttcacaccg                                                80

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caaatatcgt ttgaatattt ttccg                                          25

<210> SEQ ID NO 9
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tattgattta gtcgtaac tacaaagaca agcaaaataa aatacgttcg ctctattaag     60
atggcaactg tgaaggataa actca                                          85

```
<210> SEQ ID NO 10
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaaaataac ataatactga aagaaagcat taagaaggcg gatgtgtcaa acaccaccgt    60
ctgtgcggta tttcacaccg                                                80

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tagattggcc gtaggggctg                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cacgcaacgc gtaagaaaca                                                20

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcggccgcga atttcttatg atttat                                         26

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagcttaagc ttgcatgccg gtagag                                         26

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggcgtatca cgaggccctt                                                20
```

```
<210> SEQ ID NO 16
<211> LENGTH: 85
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16 ttttttttagt tttaaaacac caagaactta gtttcgaata aacacacata aacaaacaaa        60
atggcaactg tgaaggataa actca                                              85

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaattaattc ttgaagacga aagggcctcg tgatacgcct agattgtact gagagtgcac        60

<210> SEQ ID NO 18
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctaagtcata aagctataaa aagaaaattt atttaaatgc aagatttaaa gtaaattcac        60
ctgtgcggta tttcacaccg                                                    80

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atttcttaaa cttcttaaat tctac                                              25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
atgaatcgaa aatgtcatta aaata                                              25
```

METHOD FOR PRODUCING CHEMICAL BY CONTINUOUS FERMENTATION

SEQUENCE LISTING

This application contains a Sequence Listing which has been submitted in ASCII format via EFS-Web and is hereby incorporated by reference in its entirety. Said ASCII copy, created on Jun. 14, 2013, is named NGB-13-1199_SL.txt and is 6,590 bytes in size.

TECHNICAL FIELD

This disclosure relates to a method of producing a chemical by continuous fermentation.

BACKGROUND

A fermentation method for producing substances which involves culturing microorganisms or cultured cells can be roughly classified into (1) a batch fermentation method and a fed-batch or semi-batch fermentation method and (2) a continuous fermentation method. The batch, fed-batch or semi-batch fermentation method has advantages such as use of simple facilities, completion of culture in a short time, and low possibility of contamination with unwanted microorganisms other than cultured ones in product fermentation using pure microorganism culture techniques. However, the concentration of the product in a culture medium increases with the passage of time, leading to reduction in productivity and yield due to inhibition of fermentation by the product or influence of an increase in osmotic pressure. Accordingly, it is difficult to maintain high yield and high productivity stably for long hours.

The continuous fermentation method, on the other hand, can keep a high yield and high productivity for longer hours than the above-mentioned batch, fed-batch or semi-batch fermentation method by preventing accumulation of an objective substance in a fermentor. Conventional continuous culture is a culture method in which a liquid amount in a fermentor is kept constant by feeding the fermentor with a fresh medium while discharging the same amount of the culture medium from the fermentor. In batch culture, culture is terminated when the initial substrate concentration vanishes as a result of consumption, whereas in continuous culture, culture can be theoretically continued infinitely.

In the conventional continuous culture, on the other hand, microorganisms together with a culture medium are discharged from a fermentor so that the concentration of microorganisms in the fermentor is hardly kept high. If the concentration of microorganisms in the fermentor can be kept high, it leads to improvement in the efficiency of fermentation production per fermentation volume. For this purpose, microorganisms should be retained or refluxed in the fermentor.

Examples of the method of retaining or refluxing microorganisms in a fermentor include a method of conducting solid-liquid separation of a discharged culture medium by centrifugal separation and returning precipitated microorganisms to a fermentor and a method of filtering the discharged culture medium to separate microorganisms as solids and discharging only the supernatant of the culture medium from a fermentor. The method using centrifugal separation is however not practical because of a high power cost. The method using filtration requires a high pressure for filtration as described above so that it has been examined mainly at a laboratory level.

There has therefore been proposed a continuous fermentation method to keep the concentration of the microorganisms or cultured cells in a culture medium high. That method includes separating microorganisms or cultured cells through a separation membrane and retaining or refluxing the microorganisms or cultured cells thus separated in a culture medium while recovering a product from the filtrate. For example, there have been disclosed technologies (JP-A-5-95778, JP-A-62-138184 and JP-A-10-174594) relating to membrane separation type continuous fermentation in a continuous fermentation apparatus using a ceramic membrane.

On the other hand, there has recently been proposed a technology of conducting continuous culture by using a continuous culture apparatus using an organic polymer separation membrane (refer to WO 07/097,260 and JP-A-2008-212138). According to that proposal, by using a continuous culture apparatus equipped with a tank for culturing microorganisms or cultured cells and a tank to conduct membrane separation between an intended fermentation product and the microorganisms or cultured cells, a variety of chemicals can be produced at a higher production rate compared with the batch, fed-batch, or semi-batch culture method.

In such continuous fermentation technologies using a separation membrane, reduction in equipment cost, a membrane exchanging cost, and an installation area has been tried by using a separation membrane excellent in water permeability to reduce the area of the membrane, thereby reducing the size of the apparatus from the standpoint of cost reduction. A hollow fiber membrane with a wide filtration area relative to its volume has attracted attentions from such a standpoint of the cost.

Such separation membranes including a hollow fiber membrane sometimes however have deteriorated filtration ability due to SS (Suspended Solids) or adsorbed material attached to the membrane surface during filtrating operation, making it impossible to secure a necessary filtrate amount. With regards to a method of suppressing clogging of the membrane with microorganisms or cultured cells, there have been made several proposals on a technology relating to cleaning of a porous separation membrane or setting of filtering conditions.

As a cleaning method of a porous separation membrane, there have been disclosed, for example, a method of backwashing a porous separation membrane with warm water (JP-A-2000-317273), a method of backwashing a porous separation membrane with a permeate of the filtration (Japanese Patent Laid-Open No. Hei JP-A-11-215980), and the like.

Moreover, it is possible to use a method of scrubbing which conducts cleaning while supplying a gas. Scrubbing cleaning has already been employed for water treatment. For example, Japanese Patent No. 3948593 has proposed a method of introducing a gas in a module and at the same time, introducing a gas or a liquid to the filtrate side of the membrane, thereby cleaning the membrane.

On the other hand, there is an example of using a gas cleaning method in a membrane bioreactor (MBR) for water treatment using high-concentration microorganisms. For example, there is known a method (JP-A-2005-88008) of supplying gas-containing raw water from a raw water supply port provided at the lower portion of a module.

The methods of cleaning a separation membrane described in JP '273 and JP '980 are methods of cleaning a porous separation membrane to be used when a fermentation product is filtered and recovered from a culture medium after completion of fermentation. If such a cleaning method is used for a continuous fermentation method which retains microorganisms or cultured cells in a culture medium after filtration treatment, it is difficult to keep the productivity of fermentation at a high level because the culture medium is diluted.

The technology proposed in JP '593 is a method of treating river surface stream water, used as objective raw water, having a turbidity of from 0.1 to 5. Substances causing clogging are different from those causing clogging during filtration of a culture medium so that this method cannot exhibit its effect fully for suppressing clogging and deterioration in filtration ability in continuous fermentation.

According to JP '008, a gas is supplied under conditions intended to satisfy only the membrane surface cleaning effect and no consideration is given to the influence of an excessively supplied gas on fermentation results and on filtration separation of a product. This means that the technology of JP '008 cannot be applied as is to the production of a chemical.

In the conventional art, an appropriate scrubbing cleaning method for continuous fermentation operation using a membrane separation technology has not been studied. There is therefore a demand for a method of enhancing the fermentation productivity of a chemical while conducting membrane surface cleaning to keep the filterability of a separation membrane.

It could therefore be helpful to provide a method for producing a chemical through continuous fermentation which method requires only a simple and easy operation but keeps high productivity stably for long hours.

SUMMARY

We found that by supplying a gas at a linear velocity of 0.15 cm/s to 70 cm/s from the lower portion of a membrane module or from a pipe communicating between a fermentor and the membrane module, it becomes possible to reduce clogging of the membrane, thereby conducting a membrane operation stably for a long period of time and at the same time, to improve fermentation performance. This enables stable production of a chemical for a long period of time. We thus provide the following:

(1) A method for producing a chemical through continuous fermentation, the method including:
    (a) culturing a cell in a culture medium in a fermentor to ferment a feedstock to produce a chemical;
    (b) conducting filtration of the culture medium by using a separation membrane module;
    (c) separating a permeate containing the chemical from the culture medium while retaining a non-permeated liquid in the fermentor, and
    (d) supplying a gas from at least one of a lower portion of the separation membrane module and a pipe communicating between the fermentor and the separation membrane module to adjust a gas linear velocity in the separation membrane module to 0.15 cm/s to 70 cm/s while supplying the separation membrane module with a liquid.
(2) The method for producing a chemical according to (1), in which in the step (d), the gas contains oxygen.
(3) The method for producing a chemical according to (2), further including, in addition to the step (d), a step (e) of supplying the fermentor with a gas, in which:
    the gas is supplied in the step (d) intermittently, and
    when the gas is not supplied in the step (d), a supply rate of the gas in the step (e) is increased compared with that when the gas is supplied in the step (d).
(4) The method for producing a chemical according to any of (1) to (3), in which the filtration in the step (b) is conducted intermittently.
(5) The method for producing a chemical according to any of (1) to (4), in which the cell is a microorganism.
(6) The method for producing a chemical according to 5, wherein the microorganism is a microorganism belonging to any of the Genus *Escherichia*, the Genus *Providencia*, the Genus *Corynebacterium*, the Genus *Brevibacterium*, and the Genus *Serratia*.
(7) The method for producing a chemical according to (6), in which the microorganism is any of *Escherichia coli*, *Providencia rettgeri*, *Corynebacterium glutamicum*, *Brevibacterium flavum*, *Brevibacterium lactofermentum*, and *Serratia marcescens*.
(8) The method for producing a chemical according to any of (1) to (4), in which the cell is a yeast.
(9) The method for producing a chemical according to any of (1) to (8), in which the chemical is an amino acid.
(10) The method for producing a chemical according to (9), in which the amino acid is L-threonine, L-lysine, L-glutamic acid, L-tryptophan, L-isoleucine, L-glutamine, L-arginine, L-alanine, L-histidine, L-proline, L-phenylalanine, L-aspartic acid, L-tyrosine, L-methionine, L-serine, L-valine, or L-leucine.
(11) The method for producing a chemical according to any of (1) to (8), in which the chemical is an organic acid.
(12) The method for producing a chemical according to (11), in which the chemical is lactic acid.
(13) The method for producing a chemical according to any of (1) to (8), in which the chemical is cadaverine.

We make it possible to stabilize the filtration property of a separation membrane for long hours, enhance the fermentation results, reduce the possibility of contamination occurring due to unwanted microorganisms other than microorganisms necessary for culturing, and to produce a chemical, which is a fermentation product, stably at a low cost widely in the fermentation industry.

DESCRIPTION OF REFERENCE NUMERALS AND SIGNS

Figure 1:
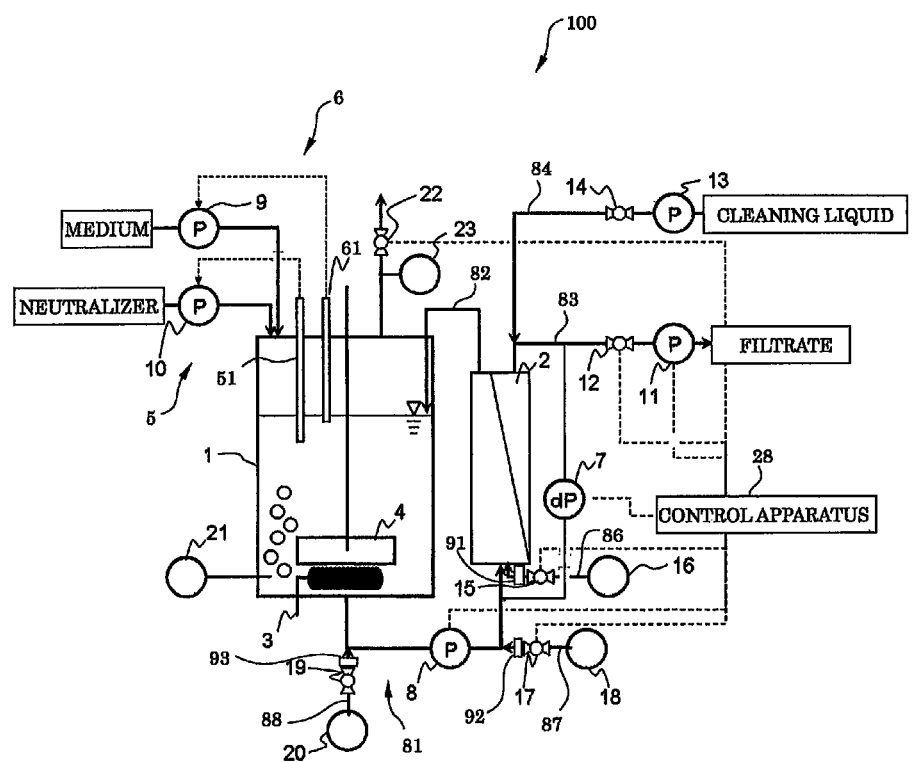
FIG. 1 is a schematic side view showing one example of a membrane separation type continuous fermentation apparatus.

1 Fermentor
2 Separation membrane module
3 Temperature control unit
4 Stirring apparatus
5 pH Control unit
6 Level control unit
7 Pressure difference control unit
8 Circulating pump
9 Medium supply pump
10 Neutralizer supply pump
11 Filtration pump
12 Filtration valve
13 Cleaning pump
14 Cleaning valve
15 Module gas supply control valve
16 Module scrubbing gas supply apparatus
17 Pipe gas supply control valve
18 Pipe scrubbing gas supply apparatus
19 Upstream-of-pump pipe gas supply control valve
20 Upstream-of-pump pipe scrubbing gas supply apparatus
21 Fermentor gas supply apparatus
22 Fermentor pressure control valve
23 Fermentor pressure gauge
28 Control unit
51 pH Sensor
61 Level sensor
81 Pipe for communicating between the fermentor 1 and the primary side of the separation membrane module 2
82 Pipe for returning a concentrate which has not passed through the separation membrane of the separation membrane module 2 to the fermentor 1
83 Pipe connected to the separation membrane module 2 for discharging a filtrate to the outside of the apparatus
84 Pipe for connecting a cleaning liquid tank and the secondary side of the separation membrane module 2
86 Pipe for connecting the module scrubbing gas supply apparatus 16 and the separation membrane module 2
87 Pipe for connecting the pipe scrubbing gas supply apparatus 18 and the pipe 81
88 Pipe for connecting the upstream-of-pump pipe scrubbing gas supply apparatus 20 and the pipe 81
91 Flow meter
92 Flow meter
93 Flow meter
100 Continuous fermentation apparatus

DETAILED DESCRIPTION

1. Continuous Fermentation Apparatus

One example of a continuous fermentation apparatus will next be described referring to FIG. 1. FIG. 1 is a schematic side view of a continuous fermentation apparatus.

As shown in FIG. 1, a continuous fermentation apparatus 100 is equipped with a fermentor 1, a separation membrane module 2, and pipes for connecting between the fermentor 1 and the separation membrane module 2. The fermentor 1 and the separation membrane module 2 are connected to each other to constitute a circulation system.

The fermentor 1 is constituted so that a culture medium can be placed therein. More specifically, the fermentor 1 is made of a material excellent in pressure resistance, heat resistance, and antifouling property. The fermentor 1 may have various shapes such as cylindrical shape and polygonal columnar shape. The fermentor 1 may have a shape permitting pouring therein of a fermentation feedstock, a cell, and a solid, liquid, or gas necessary for fermentation and stirring of the resulting mixture, and if necessary permitting sterilization, and moreover permitting hermetic sealing. From the standpoint of stirring efficiency of a culture medium, the fermentor 1 is preferably cylindrical. The fermentor 1 is preferably maintained under pressure inside to prevent microorganisms from entering inside the fermentor 1 from the outside the fermentor and proliferating therein. To control the pressure in the fermentor 1, a mechanism such as fermentor pressure gauge 23 or the like which will be described later is provided.

The separation membrane module 2 is equipped with many separation membranes such as hollow fiber membranes or flat sheet membranes. Details of the separation membrane module will be described later in detail.

The continuous fermentation apparatus 100 is equipped with a control apparatus 28. The control apparatus 28 can conduct various calculations. The control apparatus 28 controls operation of each unit in the continuous fermentation apparatus 100 based on the detection results of various sensors, input by users, and various settings.

The continuous fermentation apparatus 100 is equipped further with, as a mechanism involved mainly in a fermentation step, a fermentor gas supply apparatus 21, a fermentor pressure regulating valve 22, a fermentor pressure gauge 23, a temperature control unit 3, a stirring apparatus 4, a pH control unit 5, and a level control unit 6.

The fermentor gas supply apparatus 21 supplies a gas into the fermentor 1. The gas thus supplied may be recovered and then supplied again in the fermentor 1 by the fermentor gas supply apparatus 21.

Based on the control of the control apparatus 28, the fermentor pressure regulating valve 22 releases air from the fermentor 1 to the outside when the atmospheric pressure in the fermentor 1 detected by the fermentor pressure gauge 23 reaches the upper limit. In such a manner, the pressure inside the fermentor 1 can be maintained at an appropriate level. The pressure inside the fermentor 1 is maintained preferably at a pressure higher than the outside atmospheric pressure to prevent microorganisms from contamination in the fermentor.

The temperature control unit 3 is equipped with a temperature sensor and a temperature regulating unit. The temperature sensor detects the temperature of a culture medium in the fermentor 1. Under the control by the control apparatus 28, the temperature regulating unit works so that the detection results of the temperature sensor fall within a predetermined range. Thus, a temperature environment suited for fermentation or cell proliferation can be maintained by keeping the temperature in the fermentor 1 constant. The temperature regulating unit can have one or both of heating and cooling functions.

The stirring device 4 keeps an appropriate fermentation environment by stirring a culture medium in the fermentor 1.

The pH control unit 5 is equipped with a pH sensor 51 and a neutralizer supply pump 10. The pH sensor 51 detects the pH of a culture medium in the fermentor 1. The neutralizer supply pump 10 is placed on a pipe that connects a neutralizer tank and the fermentor 1 and adds a neutralizer to the fermentor 1. The neutralizer supply pump 10 works based on the control of the control apparatus 28 so that the detection results of the pH sensor 51 fall within a predetermined range. As the neutralizer, an acid or an alkali is used.

The level control unit 6 is equipped with a level sensor 61 and a medium supply pump 9. The medium supply pump 9 is placed on a pipe that connects a medium tank and the fermentor 1. Based on the control of the control apparatus 28, when the detection results of the level sensor 61 show that the liquid surface level of a culture medium in the fermentor 1 is below a predetermined lower limit, the medium supply pump 9 starts operation to supply a medium to the fermentor 1; and when the liquid surface reaches the upper limit, the operation of the medium supply pump 9 is terminated. Thus, the amount of a culture medium in the fermentor 1 is kept appropriate.

The continuous fermentation apparatus 100 is equipped with a circulation system that circulates a culture medium between the fermentor 1 and the separation membrane module 2. More specifically, the continuous fermentation apparatus 100 is equipped with a pipe 81 that communicates between the fermentor 1 and the primary side of the separation membrane module 2 and a pipe 82 that returns a concentrate which has not passed through the separation membrane of the separation membrane module 2 to the fermentor 1. In this example, the pipe 81 is connected to the lower portion of the separation membrane module 2 so that a culture medium is supplied to the separation membrane module 2 from the lower portion thereof. On the pipe 81 that supplies a culture medium from the fermentor 1 to the separation membrane module 2, a circulating pump 8 is placed. The circulating pump 8 works to feed a culture medium from the fermentor 1 toward the separation membrane module 2.

In addition, the continuous fermentation apparatus 100 is equipped with a pipe 83 that is connected to the separation membrane module 2 and discharges a filtrate (that is, a permeate) outside the apparatus. On this pipe 83, a filtration pump 11 is provided and between the filtration pump and the separation membrane module 2, a filtration valve 12 is provided.

The continuous fermentation apparatus 100 is equipped with a constitution for backwashing of the separation membrane module 2. The term "backwashing" means cleaning of a separation membrane by causing a liquid for cleaning (which may hereinafter be called "cleaning liquid") to pass through the separation membrane from the secondary side to the primary side thereof. The continuous fermentation apparatus 100 is equipped with a cleaning liquid tank that contains a cleaning liquid therein, a pipe 84 that connects the cleaning liquid tank and the secondary side of the separation membrane module 2, a cleaning pump 13 provided on the pipe 84, and a cleaning valve 14 provided between the cleaning pump 13 and the separation membrane module 2. By this cleaning pump 13, a cleaning liquid is delivered toward the separation membrane module 2.

The pipe 84 may have a pressure gauge, a flow meter, a sterilization apparatus, a sterilization filter, and the like.

A pressure difference control unit 7 can detect a transmembrane pressure difference (TPD) of the separation membrane module 2. In other words, it detects a pressure difference between the primary side (the side to which a culture medium is supplied) and the secondary side (the side from which a permeate, that is, a filtrate is discharged).

The continuous fermentation apparatus 100 further has a constitution involved in scrubbing. The scrubbing is a cleaning method in which a gas is supplied to the primary side of the separation membrane module and by making use of oscillation of a liquid and the gas which occurs during passage of the gas through the separation membrane module, substances attached to the surface of the separation membrane are removed therefrom.

In the continuous fermentation apparatus 100, particularly the separation membrane module 2 is supplied with a gas from at least one of the lower portion of the separation membrane module 2 and the pipe 81 communicating between the fermentor 1 and the separation membrane module 2. It is equipped with, particularly as the constitution relating to scrubbing, a gas supply source, a gas supply port, and a mechanism capable of regulating a supply rate of a gas from gas supply source.

More specifically, the continuous fermentation apparatus 100 is equipped with a module gas supply control valve 15, a module scrubbing gas supply apparatus 16, a pipe gas supply control valve 17, a pipe scrubbing gas supply apparatus 18, an upstream-of-pump pipe gas supply control valve 19, and an upstream-of pump pipe scrubbing gas supply apparatus 20.

It is to be noted that at least one gas supply sources is necessary among the module scrubbing gas supply apparatus 16, the pipe scrubbing gas supply apparatus 18, and the upstream-of-pump pipe scrubbing gas supply apparatus 20. This means that the respective constitutions with only one, only two, and all three gas supply apparatuses are embraced in the example. The module gas supply control valve 15, the pipe gas supply control valve 17, and the upstream-of-pump pipe gas supply control valve 19 are members paired with the module scrubbing gas supply apparatus 16, the pipe scrubbing gas supply apparatus 18, and the upstream-of-pump pipe scrubbing gas supply apparatus 20, respectively.

The module scrubbing gas supply apparatus 16 is connected to the primary side of the separation membrane of the separation membrane module 2, that is, to the side to which a culture medium is supplied, via a pipe 86. The pipe 86 is a pipe different from the pipe 81 via which a culture medium is supplied to the separation membrane module 2. This means that the module scrubbing gas supply apparatus 16 is connected directly to the separation membrane module 2 via a passage different from the supply route of a culture medium. In addition, the pipe 86 is connected to the lower portion of the separation membrane module 2. The term "lower portion" as used herein may mean the bottom portion of the separation membrane module or a portion of the separation membrane module within ⅓ of the height from the bottom surface. Via the pipe 86, the module scrubbing gas supply apparatus 16 can feed a gas from the lower portion of the separation membrane module 2. The module gas supply control valve 15 is placed on the pipe 86 and can regulate a gas supply amount by opening or closing the valve.

The pipe scrubbing gas supply apparatus 18 is connected, downstream of the circulating pump 8, connected to the pipe 81 via a pipe 87. The pipe gas supply control valve 17 is provided on the pipe 87 and can regulate a gas supply amount by opening or closing the valve. The pipe scrubbing gas supply apparatus 18 supplies a gas from the pipe 81 communicating between the fermentor 1 and the separation membrane module 2. When the pipe 81 is connected to the upper portion of the separation membrane module 2, the pipe scrubbing gas supply apparatus 18 can supply a gas from the upper portion of the separation membrane module 2.

The upstream-of-pump pipe scrubbing gas supply apparatus 20 is connected to the pipe 81 via a pipe 88 upstream of the circulating pump 8. The upstream-of-pump pipe gas supply control valve 19 is provided on the pipe 88 and can regulate a gas supply amount by opening or closing the valve. The upstream-of-pump pipe scrubbing gas supply apparatus 20 supplies a gas from the lower portion of the separation membrane module 2 and at the same time, supplies a gas from the pipe 81 communicating between the fermentor 1 and the separation membrane module 2. When the pipe 81 is connected to the upper portion of the separation membrane module 2, the upstream-of-pump pipe scrubbing gas supply apparatus 20 can supply a gas from the upper portion of the separation membrane module 2.

The pipes from 86 to 88 may be equipped with a sterilization apparatus or a sterilization filter to prevent unwanted microorganisms from entering the fermentor 1.

The term "gas supply port" as used herein means a portion from which a gas is released into a culture medium or a liquid. The gas supply port is preferably constituted to permit generation of bubbles capable of cleaning the membrane surface therewith. The bubbles generated may be either fine bubbles or rough bubbles. The size of the bubbles is changed by changing the shape of the gas supply port, depending on the kind of the separation membrane or conditions such as gas diffusion amount. The gas supply port may be formed by providing a pipe made of polyvinyl chloride or stainless with an air discharge hole or a diffuser tube using a porous rubber, ceramic, or membrane may be used. The size of the gas supply port is not limited insofar as it can supply a specified amount of a gas and at the same time, is large enough not to cause clogging with a fermentation liquid. The gas supply port may be equipped with a sterilization filter to prevent unwanted microorganisms from entering the fermentation system.

In FIG. 1, the gas supply port is provided at the end portion, of two end portions of each of the pipes 86 to 88, on the side near the separation membrane module 2. In other words, the pipes 86 to 88 are pipes connecting from the gas supply source to the gas supply port.

Thus, in FIG. 1, the gas supply port may be provided in the lower portion of the separation membrane module. In the constitution of supplying a culture medium from the fermentor to the separation membrane module via a pump, it may be provided either between the fermentor and the pump or between the pump and the separation membrane module.

As an example of a mechanism that measures a linear velocity of a gas supplied by scrubbing, flow meters 91, 92, and 93 are shown in FIG. 1. The flow meter 91 is disposed in the pipe 86 and can measure the flow rate of a gas passing in the pipe 86. The flow meter 91 is utilized for measurement of the linear velocity of a gas supplied by the module scrubbing gas supply apparatus 16. The flow meter 92 is disposed in the pipe 87 and can measure the flow rate of a gas passing in the pipe 87. The flow meter 92 is utilized for measurement of the linear velocity of a gas supplied from the pipe scrubbing gas supply apparatus 18. The flow meter 93 is disposed in the pipe 88 and can measure the flow rate of a gas passing in the pipe 88. The flow meter 93 is utilized for measurement of the linear velocity of a gas supplied by the upstream-of-pump pipe scrubbing gas supply apparatus 20.

2. Separation Membrane Module

The separation membrane module includes a separation membrane and a case for housing the separation membrane therein.

The separation membrane to be used for the separation membrane module may be either an organic membrane or an inorganic membrane. The separation membrane is not limited insofar as it is a membrane usable for filtration of a culture medium and having durability against cleaning with a gas. Examples of the separation membrane include membranes made of polyvinylidene fluoride, polysulfone, polyethersulfone, polytetrafluoroethylene, polyethylene, polypropylene, and ceramics. Of these, separation membranes made of polyvinylidene fluoride are particularly preferred because they are resistant to fouling with a fermentation liquid, can be easily cleaned, and are excellent in durability against cleaning with a gas.

The separation membrane is preferably a porous film having pores with an average pore size of 0.001 μm or greater but less than 10 μm to effectively separate the cells in the fermentation liquid. The separation membrane may have any shape and either of a flat sheet membrane or a hollow fiber membrane can be used, but the hollow fiber membrane having a great membrane area relative to the volume of the module is preferred. The average pore size of the membrane is determined according to the method described in ASTM: F316-86 (another name: half dry method). What is determined by this half dry method is the average pore size of a minimum pore layer of a membrane.

The following are standard measurement conditions of an average pore size when the half dry method is used:
Liquid used: ethanol
Measurement temperature: 25° C.
Pressure rising rate: 1 kPa/sec.

The average pore size [μm] is determined from the following equation:

$$\text{Average pore size [μm]} = (2860 \times \text{surface tension [mN/m]})/\text{half dry air pressure [Pa]}.$$

The surface tension at 25° C. of ethanol is 21.97 mN/m (The Chemical Society of Japan, Kagaku Binran Kisohen Kaitei 3rd Edition, p. 11-82, Maruzen, 1984) so that under the standard measurement conditions, the average pore size can be determined from the following equation:

$$\text{Average pore size [μm]} = 62834.2/(\text{half dry air pressure [Pa]}).$$

The outer diameter of an external pressure type hollow fiber membrane is preferably 0.5 mm to 3 mm. When the outer diameter is 0.5 mm or greater, resistance of the filtrate flowing in the hollow fiber membrane can be suppressed to a relatively low level. When the outer diameter is 3 mm or less, on the other hand, the hollow fiber membrane can be prevented from being collapsed by the outer pressure due to the fermentation liquid or gas.

The inner diameter of an inner pressure type hollow fiber membrane is preferably 0.5 mm to 3 mm. When the inner diameter is 0.5 mm or greater, resistance of a fermentation liquid flowing in the hollow fiber membrane can be suppressed to a relatively low level. When the inner diameter is 3 mm or less, on the other hand, an increase in the number of modules used can be suppressed because a membrane surface area can be secured.

The case of the separation membrane module is made of a material excellent in pressure resistance and the shape of it is not limited insofar as it enables supply of a fermentation liquid to the primary side of the module. Examples include cylindrical shape and polygonal columnar shape. In consideration of the flow of the fermentation liquid and handling property, the case has preferably a cylindrical shape.

3. Method of Producing Chemical

The production method may be a method of producing a chemical through continuous fermentation and has the following steps (a) to (d):
(a) culturing cells in a culture medium in a fermentor to ferment a feedstock to prepare a chemical;

(b) conducting filtration of the culture medium by using a separation membrane module;

(c) separating a permeate containing the chemical from the culture medium while retaining a non-permeated liquid in the fermentor, and (d) supplying a gas from at least one of a lower portion of the separation membrane module and a pipe communicating between the fermentor and the separation membrane module to adjust a gas linear velocity in the separation membrane module to 0.15 cm/s to 70 cm/s while supplying the separation membrane module with a liquid.

A description will next be made on each step. It is to be noted that the steps (a) to (c) may be called continuous cell culture steps or continuous fermentation steps.

3-1. (a) Step of Preparing Chemical

Cells

The "cells" as used herein means a concept including microorganisms, cultured cells, eukaryotic cells, and prokaryotic cells. Examples of the microorganisms include yeasts popularly used in the fermentation industry such as baker's yeast; microorganisms such as *Escherichia coli*, lactic acid microorganisms, and coryneform microorganisms; filamentous microorganisms; and actinomycete. The cultured cells are cells derived from multicellular organisms and examples thereof include animal cells and insect cells. The cells to be used for the production of a chemical may be either those isolated from a natural environment or those having some properties altered by mutation or gene recombination.

The eukaryotic cells have therein a structure called cell nucleus (nucleus) and clearly discriminated from prokaryotic organisms having no cell nucleus (which will hereinafter be called "nucleus" simply). For the production of a chemical, yeasts are preferably used among eukaryotic cells. Examples of the yeasts suited for the production of a chemical include yeasts belonging to Genus *Saccharomyces* and yeasts belonging to *Saccharomyces cerevisiae*.

The prokaryotic cells do not have therein a structure called "cell nucleus (nucleus)" and are clearly discriminated from eukaryotic cells having a cell nucleus (nucleus). For the production of a chemical, lactic acid microorganisms are preferred among prokaryotic cells.

Cells are selected depending on a chemical to be prepared, feedstock, culture conditions, and the like.

Examples of cells producing L-amino acids include microorganisms popularly used in the fermentation industry such as *Escherichia coli* and coryneform microorganisms.

More specifically, examples of L-threonine producing microorganisms include microorganisms belonging to Genus *Escherichia*, Genus *Providencia*, Genus *Corynebacterium*, Genus *Brevibacterium*, and Genus *Serratia*. Of these, *Escherichia coli*, *Providencia rettgeri*, *Corynebacterium glutamicum*, *Brevibacterium flavum*, *Brevibacterium lactofermentum*, and *Serratia marcescens* are particularly preferred.

Examples of the L-lysine producing microorganisms include microorganisms belonging to Genus *Escherichia*, Genus *Corynebacterium*, and Genus *Brevibacterium*. Of these, *Escherichia coli*, *Corynebacterium glutamicum*, *Brevibacterium flavum*, and *Brevibacterium lactofermentum* are particularly preferred.

As L-glutamic acid producing microorganisms, *Corynebacterium glutamicum*, *Brevibacterium flavum*, and *Brevibacterium lactofermentum* are preferred.

Examples of L-tryptophan producing microorganisms include *Corynebacterium glutamicum*, *Brevibacterium flavum*, *Brevibacterium lactofermentum*, *Bacillus subtilis*, *Bacillus amyloliquefaciens*, and *Escherichia coli*.

Examples of L-isoleucine producing microorganisms include *Corynebacterium glutamicum*, *Brevibacterium flavum*, *Brevibacterium lactofermentum* and *Serratia marcescens*.

Examples of L-glutamine producing microorganisms include *Corynebacterium glutamicum*, *Brevibacterium flavum*, *Brevibacterium lactofermentum*, and *Flavobacterium rigense*.

Examples of L-arginine producing microorganisms include *Corynebacterium glutamicum*, *Brevibacterium flavum*, *Serratia marcescens*, *Escherichia coli*, and *Bacillus subtilis*.

Examples of L-alanine producing microorganisms include *Brevibacterium flavum* and *Arthrobacter oxydans*.

Examples of L-histidine producing microorganisms include *Corynebacterium glutamicum*, *Brevibacterium flavum*, *Brevibacterium ammoniagenes*, *Serratia marcescens*, *Escherichia coli*, *Bacillus subtilis*, and *Streptomyces coelicolor*.

Examples of L-proline producing microorganisms include *Corynebacterium glutamicum*, *Kurthia catenaforma*, *Serratia marcescens*, and *Escherichia coli*.

Examples of L-phenylalanine producing microorganisms include *Corynebacterium glutamicum*, *Brevibacterium flavum*, *Brevibacterium lactofermentum*, and *Escherichia coli*.

Examples of L-aspartic acid producing microorganisms include *Brevibacterium flavum*, *Bacillus megatherium*, *Escherichia coli*, and *Pseudomonas fluorescens*.

Examples of L-tyrosine producing microorganisms include *Corynebacterium glutamicum*, *Brevibacterium flavum*, *Brevibacterium lactofermentum*, and *Escherichia coli*.

As L-methionine producing microorganisms, *Corynebacterium glutamicum* is preferred.

Examples of serine producing microorganisms include *Corynebacterium glutamicum*, *Brevibacterium flavum*, *Brevibacterium lactofermentum*, and *Arthrobacter* oxydans.

Examples of L-serine producing microorganisms include *Corynebacterium acetoacidophilum* and *Brevibacterium lactofermentum*.

Examples of L-valine producing microorganisms include *Brevibacterium lactofermentum*, *Serratia marcescens*, and *Klebsiella pneumoniae*.

Examples of L-leucine producing microorganisms include *Corynebacterium glutamicum*, *Brevibacterium lactofermentum*, and *Serratia marcescens*.

The microorganisms having production ability of an L-amino acid may be isolated from the natural environment or have some properties modified by mutation or gene recombination. Examples include *Providencia rettgeri* having improved L-threonine productivity, described in JP-A-2-219582 and *Corynebacterium glutamicum* having improved L-alanine productivity, described in JP-T-3-500486.

Separation and purification of an L-amino acid contained in a culture medium can be conducted using conventionally known methods such as filtration, concentration, distillation, and crystallization in combination.

For the production of lactic acid, yeast is preferred as the eukaryotic cell and lactic acid microorganisms are preferred as the prokaryotic cell. Of these, the yeast obtained by introducing a gene encoding lactate dehydrogenase into cells is preferred. In particular, lactic acid microorganisms showing preferably a yield, relative to glucose consumption, of 50% or more, more preferably a yield, relative to glucose consumption, of 80% or more are preferred. The term "yield relative to glucose consumption" means a ratio (weight ratio) of the production amount of lactic acid relative to the amount of glucose consumed.

Examples of lactic acid microorganisms include wild-type strains having ability of synthesizing lactic acid such as microorganisms belonging to Genus *Lactobacillus*, Genus *Bacillus*, Genus *Pediococcus*, Genus *Tetragenococcus*, Genus *Carnobacterium*, Genus *Vagococcus*, Genus *Leuconostoc*, Genus *Oenococcus*, Genus *Atopobium*, Genus *Streptococcus*, Genus *Enterococcus*, Genus *Lactococcus*, and Genus *Sporolactobacillus*.

Lactic acid microorganisms having a high yield of lactic acid relative to glucose consumption or lactic acid microorganisms capable of providing lactic acid with high optical purity can be selected and used. Examples of lactic acid microorganisms having ability of producing D-lactic acid selectively include D-lactic acid producing microorganisms belonging to Genus *Sporolactobacillus*. Preferred specific examples include *Sporolactobacillus laevolacticus* and *Sporolactobacillus inulinus*. More preferred examples include *Sporolactobacillus laevolacticus* AT 23492, ATCC 23493, ATCC 23494, ATCC23495, ATCC 23496, ATCC 223549, IAM12326, IAM12327, IAM 12328, IAM 12329, IAM 12330, IAM 12331, IAM 12379, DSM 2315, DSM 6477, DSM 6510, DSM 6511, DSM 6763, DSM 6764, and DSM 6771 and *Sporolactobacillus inulinus* JCM 6014.

Examples of lactic acid microorganisms having a high yield of L-lactic acid relative to glucose consumption include *Lactobacillus yamanashiensis, Lactobacillus animalis, Lactobacillus agilis, Lactobacillus aviaries, Lactobacillus casei, Lactobacillus delbruekii, Lactobacillus paracasei, Lactobacillus rhamnosus, Lactobacillus ruminis, Lactobacillus salivarius, Lactobacillus sharpeae, Pediococcus dextrinicus*, and *Lactococcus lactis*. These microorganisms can be selected and used for producing L-lactic acid.

For the production of D-lactic acid, wild-strain type cells having reinforced enzyme activity of D-lactate dehydrogenase (which may hereinafter be called "DLDH") are also preferably used. For enhancing enzyme activity, a conventionally known chemical mutagenesis can also be employed. The enzyme activity of D-lactate dehydrogenase can also be enhanced by incorporating, in cells, a gene encoding D-lactate dehydrogenase. This means that recombinant cells are also preferably used for the production of a chemical.

When D-lactic acid is produced using recombinant cells, *Escherichia coli* and lactic acid microorganisms are preferred as prokaryotic cells, while yeasts are preferred as eukaryotic cells. Of these, yeasts are particularly preferred.

As a gene encoding D-lactate dehydrogenase, genes derived from *Lactobacillus plantarum, Pediococcus acidilactici*, and *Bacillus laevolacticus* are preferred, with genes derived from *Bacillus* laevolacticus being more preferred.

When L-lactic acid is produced, cells artificially imparted with lactic acid production ability or cells having artificially enforced lactic acid production ability can be used. For example, cells imparted with L-lactic acid production ability or having enforced l-lactic acid production ability can be obtained by introducing an L-lactate dehydrogenase gene (which may herein-after be called "L-LDH") into cells. As a method of imparting cells with L-lactic acid production ability or enforcing this ability, a conventionally known method of chemical mutagenesis can be used. Cells with enforced L-lactic acid production ability can also be obtained by incorporating L-LDH in the cells. This means that recombinant cells are used preferably.

When L-lactic acid is produced using recombinant cells, prokaryotic cells such as *Escherichia coli* and lactic acid microorganisms and eukaryotic cells such as yeasts are preferred as host cells, with yeasts being particularly preferred. Of the yeasts, those belonging to Genus *Saccharomyces* are preferred, with *Saccharomyces cerevisiae* being more preferred.

The sequence of L-LDH is not limited to a specific sequence insofar as it encodes a protein having activity of converting reduced nicotinamide adenine dinucleotide (NADH) and pyruvic acid into oxidized nicotinamide adenine dinucleotide (NAD+) and L-lactic acid, respectively. For example, as L-LDH, a gene derived from lactic acid microorganisms having a high yield relative to glucose consumption, a gene derived from mammals, or a gene derived from frog can be used. As the gene derived from mammals, L-LDH derived from *Homo sapiens* is preferred. As the frog-derived gene, L-LDH derived from a frog belonging to Pipidae is particularly preferred. Moreover, L-LDH derived from *Xenopus laevis*, among frogs belonging to Pipidae, is preferably used.

The human- or frog-derived L-LDH includes mutant-type genes such as genetically polymorphic genes and mutagenic genes. The term "genetically polymorphic genes" means genes having a base sequence partially changed due to natural mutagenesis on the genes. The term "mutagenic genes" means genes having mutation introduced therein artificially. Mutagenesis can be achieved for example by a method using a kit for introducing site-specific mutagenesis (Mutan-K (product of Takara Bio)) or a method using a kit for introducing random mutagenesis (BD Diversify PCR Random Mutagenesis (product of CLONTECH). The human- or frog-derived L-LDH may have a deletion or insertion in a part of the base sequence thereof insofar as it encodes a protein having activity of converting NADH and pyruvic acid into NAD+ and L-lactic acid, respectively.

A description will next be made on the production of pyruvic acid. Examples of cells producing pyruvic acid include microorganisms belonging to Genus *Pseudomonas*, Genus *Corynebacterium*, Genus *Escherichia*, and Genus *Acinetobacter*. Microorganisms such as *Pseudomonas fuluorescens, Pseudomonas aeruginosa*, and *Escherichia coli* are more preferred. Microorganisms having properties partially modified by mutation or genetic recombination may also be used. For example, microorganisms obtained by mutating or deleting an ATPase gene involved directly in ATP production by oxidative phosphorylation are also preferably used.

Molds and yeasts are also preferred. Examples include molds and yeasts belonging to Genus *Saccharomyces*, Genus *Toluropusis*, Genus *Candida*, and Genus *Schizophyllum*. More preferably, molds and yeasts belonging to *Saccharomyces cerevisiae, Saccharomyces copsis, Candida glabrata, Candida lipolytica, Toluropusis glabrata*, and *Schizophyllum commune* can be used to produce pyruvic acid.

Separation and purification of pyruvic acid contained in a culture medium can be conducted by a method using filtration and an anion exchange column. For example, a purification method using a weakly basic ion exchanger described in JP-A-6-345683 can be preferably used.

A description will next be made on the production of succinic acid. As succinic acid producing cells, for example, microorganisms belonging to Genus *Anaerobiospirillum* and Genus *Actinobacillus* can be preferably used. Specific examples thereof include *Anaerobiospirillum succiniciproducens* described in U.S. Pat. No. 5,143,833 and *Actinobacillus succinogenes* disclosed by James B. Mckinlay, et al. (*Applied and Environmental Microbiology*, 71, 6651-6656 (2005)). In addition, coryneform microorganisms such as those belonging to Genus *Corynebacterium* and Genus *Brevi-* bacterium and *Escherichia Coli* can also be used. Of the coryneform microorganisms, *Corynebacterium glutamicum*, *Brevibacterium flavum*, and *Brevibacterium lactofermentum* are preferred.

Productivity of succinic acid can be improved by using microorganisms having succinic acid production ability improved by genetic recombination. Examples of such microorganisms include lactate dehydrogenase-deficient *Brevibacterium flavum* MJ233AB-41(FERM BP-1498) described in JP-A-2005-27533, *Corynebacterium glutamicum*, and *Escherichia coli* AFP111 strains which have lacked pyruvate formate lyase and lactate dehydrogenase-deficient, described in U.S. Pat. No. 5,770,435.

A description will next be made on the production of itaconic acid. As cells usable for producing itaconic acid, for example, molds and yeasts are preferably used. Molds belonging to Genus *Aspergillus* or Genus *Ustilago* or yeasts belonging to Genus *Candida* or Genus *Rhodotorula* are more preferred. Of these, molds such as *Aspergillus terreus*, *Aspergillus itaconicus*, *Ustilago maydis*, *Ustilago cynodontis*, and *Ustilago rabenhorstina*, and *Candia Antarctica* can be preferably used in production of itaconic acid.

A description will next be made on the production of cadaverine. As cells usable for the production of cataverine, microorganisms having enhanced enzyme activity of a lysine decarboxylase and/or a lysine cadaverine antiporter are preferred, of which recombinant microorganisms having, incorporated therein, a gene encoding lysine decarboxylase and/or a lysine cadaverine antiporter are more preferred and recombinant microorganisms having, incorporated therein, one or more genes encoding lysine decarboxylase still more preferred.

When cadaverine is produced, the recombinant microorganisms are preferably *Escherichia coli* and coryneform microorganisms, more preferably coryneform microorganisms having lysine decarboxylase activity and having at least one property selected from homoserine auxotrophy and S-(2-aminoethyl)-L-cysteine resistance. The microorganisms are more preferably those deficient in homoserine dehydrogenase activity, still more preferably those made deficient in homoserine dehydrogenase activity due to mutation with an inserted gene. In addition, Genus coryneform microorganisms is preferably at least one genus selected from the group consisting of Genus *Corynebacuterium* and Genus *Brevibacterium*, with *Corynebacuterium gulutamicum* being still more preferred.

Medium

The term "fermentation feedstock" (which will hereinafter be called "feedstock" simply) means a substance from which an intended chemical is obtained through fermentation. The feedstock may be changed depending on cells, culture conditions, and the intended chemical product.

The medium to be used for culture contains, as well as the feedstock, components capable of accelerating growth of cells to smoothly produce a chemical which is an intended fermentation product. The term "medium" as used herein means a liquid medium unless otherwise specifically indicated. The medium contains, for example, a carbon source, a nitrogen source, and inorganic salts, and according to the necessity, amino acids and organic trace nutrients such as vitamins.

Examples of the carbon source include sugars such as glucose, sucrose, fructose, galactose and lactose; starches containing these sugars, starch hydrolysates, sweet potato molasses, sugar beet molasses, and sugarcane juice; extracts or concentrates of sugar beet molasses or sugarcane juice; syrups (Hi Test molasses); raw material sugars obtained by purifying or crystallizing sugar beet molasses or sugarcane juice; purified sugars obtained by purifying or crystallizing sugar beet molasses or sugarcane juice; organic acids such as acetic acid and fumaric acid; alcohols such as ethanol; and glycerin. The term "sugars" as used herein means carbohydrates which are the first oxidation products of polyvalent alcohols, have one aldehyde group or ketone group, and are classified into aldoses, that is, aldehyde-containing sugars and ketoses, that is, ketone-containing sugars.

Examples of the nitrogen source include ammonia gas, ammonia water, ammonium salts, urea, nitrates, and other organic nitrogen sources to be auxiliary used, for example, oil cakes, soybean hydrolysates, casein hydrolysates, other amino acids, vitamins, corn steep liquor, yeasts or yeast extracts, meat extracts, peptides such as peptone, and various fermented cells and hydrolysates thereof.

As the inorganic salts, phosphates, magnesium salts, calcium salts, iron salts, manganese salts, and the like can be used as needed.

Culture Medium

A culture medium contains a medium and cells cultured therein and also may contain a chemical produced as a result of the culture.

The filtrate obtained using the separation membrane module does not substantially contain cells, but for convenience of description, the filtrate may also be called "culture medium."

Culture

In the continuous fermentation apparatus 100, continuous culture is conducted by withdrawing a culture medium from the fermentor 1 while introducing a fermentation feedstock in the fermentor 1.

After batch culture or fed-batch culture is conducted at the initial stage of culture to increase the cell concentration, continuous culture may be started. At this time, the cells may be withdrawn as needed. In producing a chemical, after increase in the cell concentration, highly concentrated cells are inoculated and continuous culture may be conducted along with starting of culture.

A description will be made on the introduction of the feedstock. In FIG. 1, due to the operation of the medium supply pump 9 during culture, a medium is introduced in the fermentor 1 and as a result, the feedstock is introduced.

While culture is conducted, introduction of the feedstock may be continued without terminating it or introduction of the feedstock and termination thereof may be switched depending on the situation. For example, as described above, the initiation and termination of the introduction of a medium may be conducted based on the detection results of the level sensor 61 or it may be conducted at regular time intervals based on the measuring results using a timer, which is not illustrated. Both the automatic and manual introductions of the feedstock are included in the technical scope of our methods.

Next, a description will be made on the withdrawal of a culture medium. To achieve efficient productivity, the concentration of cells in a culture medium is preferably maintained high to the extent that the environment of the culture medium becomes inappropriate for the proliferation of microorganisms or cultured cells to increase the proportion leading to death.

In the continuous fermentation apparatus 100, continuous culture can be conducted while withdrawing a culture medium to recover a chemical by using a circulation system and keeping the concentration of cells high. Withdrawal of a culture medium by using a circulation system will be described later in detail.

A passage for withdrawal as well as the pipe 81 connected to the separation membrane module 2 may be connected to the fermentor 1 and withdrawal of a culture medium may be conducted by this passage for withdrawal. At this time, not only a liquid portion of the culture medium but also cells may be withdrawn.

During culture, fresh cells may be introduced into the fermentor 1. The cells may be introduced either manually or automatically.

In the fermentor, supply of the feedstock and initiation of withdrawal of the culture medium may not necessarily be conducted simultaneously. Supply of the feedstock and withdrawal of a culture medium may be conducted successively or intermittently.

For administrative convenience, it is usually preferred to conduct a continuous culture operation in a single fermentor. The number of fermentors is however not limited insofar the method employed is a continuous fermentation culture method in which a product is formed while proliferating cells. A plurality of fermentors may be used when the fermentor has a small capacity. In this case, high productivity can be attained even by conducting continuous culture in a plurality of fermentors connected in parallel or in series via pipes.

In the continuous fermentation apparatus 100 shown in FIG. 1, a culture medium in the fermentation apparatus 1 is stirred by a stirring apparatus 4 and conditions suited for fermentation are maintained by the temperature control unit 3, the pH control unit 5, the level control unit 6, the fermentor gas supply apparatus 21, and the like.

Culturing of cells can be conducted usually at pH of 3 to 10 and a temperature of 15° C. to 65° C. The pH of the culture medium is adjusted within a predetermined range in the above-mentioned range with an inorganic or organic acid or an alkaline substance, or moreover with urea, calcium hydroxide, calcium carbonate, ammonia gas, or the like. In the continuous fermentation apparatus 100, under the control of the control apparatus 28, the pH is automatically controlled by the pH control unit 5, while the temperature is automatically controlled by the temperature control unit 3.

3-2. Filtration Step (b) of Culture Medium

A filtration step enables continuous recovery of a chemical from a culture medium and also continuation of culture. More specifically, in FIG. 1, a culture medium is withdrawn from the fermentor 1 by the circulating pump 8, flows through the pipe 81, and supplied to the separation membrane module 2. The culture medium is separated into a concentrate and a permeate by the separation membrane module 2.

The pump 8 shown in FIG. 1 corresponds to a cross-flow circulating pump and cross-flow filtration is conducted in the separation membrane module 2. Our methods are not limited to this and dead end filtration may be used as a membrane filtration method. In the continuous fermentation operation, however, a large amount of foulants such microorganisms is attached to the membrane so that cross-flow filtration is preferred to effectively remove these foulants. When cross-flow filtration is employed, the foulants can be removed by making use of shearing force of the culture medium. Higher cleaning efficiency can be achieved by using this cross-flow filtration and scrubbing in combination.

A driving force of filtration may be obtained using a syphon making use of a level difference (water head difference) between the fermentor and the separation membrane module or obtained using a transmembrane pressure difference which occurs by the cross-flow circulating pump. As the driving force of filtration, a suction pump may be disposed on the filtrate side of the separation membrane module. In the example shown in FIG. 1, the filtration pump 11 corresponds to a suction pump.

When the cross-flow circulating pump is used, a transmembrane pressure difference can be controlled by the pressure of a suction pump. The transmembrane pressure difference can also be controlled by the pressure of a gas or liquid to be introduced to the primary side of the separation membrane module. A difference between the pressure on the primary side of the separation membrane module and the pressure on the filtrate side is detected as the transmembrane pressure difference and based on this transmembrane pressure difference, control of the pump and the like can be conducted.

In the constitution of FIG. 1, a culture medium is supplied from the fermentor 1 to the separation membrane module 2 by the circulating pump 8. The operation of the circulating pump 8 and filtration pump 11 is controlled depending on the transmembrane pressure difference detected by the pressure difference control unit 7 and, as a result, an amount of a culture medium to be supplied to the separation membrane module 2 is regulated properly.

Filtration can be conducted either continuously or intermittently. When filtration is conducted intermittently, filtration can be terminated for a predetermined time (for example, from 0.1 to 10 minutes) whenever filtration is conducted continuously, for example, for from 5 to 120 minutes. More preferably, filtration is terminated for from 0.25 to 3 minutes whenever filtration is continued for from 5 to 10 minutes. As will be described later, scrubbing may be conducted either during termination of filtration or during filtration.

3-3. Separation and Circulation Step (c)

Cells in the culture medium are not permeated through the separation membrane so that the concentrate (liquid which has remained without being permeated through the separation membrane) that has passed through the separation membrane module 2 has an increased cell concentration. Since the concentrate is returned to the fermentor 1 by the pipe 82, the cells are retained in the fermentor 1. The filtrate which has passed through the separation membrane of the separation membrane module 2 is discharged outside the apparatus by the pipe 83.

Thus, the cell concentration in the fermentor 1 is maintained high and a chemical is separated from the culture system continuously.

3-4. First Gas Supply Step (d)

The first gas supply step (d) is conducted as scrubbing cleaning in the constitution of FIG. 1. As described above, in the constitution shown in FIG. 1, a scrubbing gas is supplied by any one or more of the module scrubbing gas supply apparatus 16, the pipe scrubbing gas supply apparatus 18, and the upstream-of-pump pipe scrubbing gas supply apparatus 20. With the gas thus supplied, foulants are removed from the separation membrane in the separation membrane module.

When scrubbing is started, at least one of the module gas supply control valve 15, the pipe gas supply control valve 17, and the upstream-of-pump pipe gas supply control valve 19 is opened either by the control with the control apparatus 28 or manually. When scrubbing is terminated, these valves are closed similarly by the control with the control apparatus 28 or manually.

During scrubbing, a liquid is supplied to the separation membrane module. A high cleaning effect can be produced by the combination of a cleaning effect by scrubbing and a cleaning effect by the liquid flow in the separation membrane module.

Particularly in the constitution shown in FIG. 1, a culture medium is supplied from the fermentor 1 to the separation membrane module 2 during scrubbing. More specifically, while a scrubbing gas is supplied, the circulating pump 8 is operated. At this time, the filtration pump 11 may be terminated and at the same time, the filtration valve 12 may be closed. Filtration may be terminated. Alternatively, the filtration pump 11 may be operated and at the same time, the filtration valve 12 may be opened.

Thus, a high cleaning effect can be produced by the shearing force derived from the flow of a culture medium and the cleaning effect by scrubbing. It is to be noted that the liquid supplied to the separation membrane module at the time of gas supply is not limited to a culture medium. In addition to the culture medium, for example, a liquid not inhibiting fermentation such as a medium not containing cells can be used.

Examples of the gas usable for scrubbing include a compressed gas supplied by a gas cylinder, blower, compressor, or pipe. This means that, as the module scrubbing gas supply apparatus 16, the pipe scrubbing gas supply apparatus 18, and the upstream-of-pump pipe scrubbing gas supply apparatus 20, usable is an apparatus capable of compressing a gas while supplying the gas at a predetermined pressure or a tank capable of housing a compressed gas therein and supplying the gas at a predetermined pressure.

When aerobic fermentation is conducted in the fermentor 1, the gas supplied by scrubbing is preferably an oxygen-containing gas and it may be pure oxygen. The concentration of oxygen can be regulated by mixing a gas not adversely affecting fermentation such as air, nitrogen, carbon dioxide, methane or a mixed gas thereof. To increase a supply rate of oxygen, usable is a means of keeping the oxygen concentration at 21% or greater by adding oxygen to the air, applying a pressure to a culture medium, elevating a stirring rate, or elevating an aeration rate.

On the other hand, when anaerobic fermentation is conducted in the fermentor 1 and if a supply rate of oxygen should be reduced, it is also possible to supply a mixture of the air with an oxygen-free gas such as carbon dioxide, nitrogen, methane, or argon.

The linear velocity of the gas to be supplied to the separation membrane module is a supply amount of the gas per cross-sectional area of the membrane module and is determined according to the following Equation (1):

$$\text{Gas linear velocity (m/s)} = \text{gas supply amount (m}^3\text{/s)} \times 100 \div (\text{internal cross-sectional area of the separation membrane module (m}^2) \times (100 - \text{membrane filling ratio (\%)})) \quad (1).$$

For example, the separation membrane module is equipped with a cylindrical container having an inner radius R and (a) pieces of hollow fiber membranes housed in the container and having an outer radius of r, the internal cross-sectional area of the separation membrane module is $\pi R^2$, and the membrane filling ratio is represented by $(a \times r^2 \div R^2 \times 100)$. The membrane filling ratio of a flat sheet membrane module can also be calculated based on the cross-sectional area of a container (that is, an internal cross-sectional area of the module), the cross-sectional area of the flat sheet membrane, and the number of the flat sheet membranes.

In the control apparatus 28 in the constitution of FIG. 1, the linear velocity of a gas to be supplied to the separation membrane module 2 can be determined by turning the gas supply amount measured in the flow meter 91, 92, or 93 into the above equation (1). The control apparatus 28 can control the opening or closing of the valve 15, 17, or 19 so that the gas linear velocity falls within the above-described range.

When the scrubbing gas is supplied only by the module scrubbing gas supply apparatus 16, the gas supply rate is regulated by opening or closing the valve 15 based on the detection results of the flow meter 91. When the gas is supplied by the pipe scrubbing gas supply apparatus 18, the gas supply rate is regulated by opening or closing the valve 17 based on the detection results of the flow meter 92. When the gas is supplied from the upstream-of-pump pipe scrubbing gas supply apparatus 20, the gas supply rate is regulated by opening or closing the valve 19 based on the detection results of the flow meter 93.

Regulation of the gas linear velocity may be automatically controlled using the control apparatus 28 and an automatic valve or may be manually controlled using a manual valve.

At the gas linear velocity of 0.15 cm/s or greater, scrubbing is effective and also stirring of a culture medium, oxygen supply, and the like caused by gas supply are effective. As described above, the continuous fermentation apparatus 100 is equipped with the valve 22 and a discharge port for transferring the air to the outside from the fermentor 1. An excessively large gas linear velocity increases a foaming amount of a culture medium and tends to cause problems such as generation of contamination due to foams overflowing from the discharge port and misdetection, by the level sensor, of the position of the liquid surface in the fermentor 1 due to foams so that the gas linear velocity is preferably 70 cm/s or less.

Scrubbing cleaning is effective for removal of foulants such as cells attached to the surface of the separation membrane. Scrubbing cleaning is also effective for improving a fermentation efficiency. The gas supplied by scrubbing comes into contact with a culture medium, flows in a pipe while coming into contact with a fermentation liquid, comes into contact with a separation membrane and oscillates the membrane in the separation membrane module, flows from the separation membrane module to the fermentor while coming into contact with the fermentation liquid in a pipe, is stirred in the fermentor, and then rises to a space above the surface of the fermentation liquid to complete the contact with the fermentation liquid. On the other hand, when a gas is supplied directly to the fermentor, the gas stirred in the fermentor immediately rises to a space above the surface of the fermentation liquid to complete the contact with the fermentation liquid.

No specific limitation is imposed on the scrubbing conditions, that is, timing of scrubbing, frequency, time per scrubbing, and the like. Scrubbing conditions can be changed depending on various conditions such as transmembrane pressure difference, change in transmembrane pressure difference, pressure in the fermentor, kind of a gas to be supplied, kind of cells to be cultured, kinds of a chemical to be produced, and kind of feedstock. For example, scrubbing may be conducted successively, at intervals of a predetermined time after completion of previous scrubbing, or whenever a supply amount of a culture medium to the separation membrane module 2, that is, a filtration amount or a transmembrane pressure difference reaches a predetermined value. The continuous fermentation apparatus 100 may be equipped with a measuring device such as timer, which is not illustrated, to determine the starting or terminating time of scrubbing.

For example, scrubbing cleaning frequency is preferably 0.1 time/hour to 360 times/hour, more preferably 12 times/hour to 120 times/hour. Scrubbing cleaning frequencies of 360 times/hour or more hardly cause problems such as inconveniences due to foaming of a culture medium, damage to a filtration membrane, and an increase in operation cost. Scrubbing cleaning frequencies of 0.1 time/hour or more, on the other hand, enable to achieve a sufficient cleaning effect and prevent contamination of unwanted microorganisms because the pressure in the fermentor can be kept sufficiently high.

Scrubbing cleaning time/once can be determined, depending on the scrubbing cleaning frequency, a transmembrane pressure difference, a change in transmembrane pressure difference, a pressure in the fermentor, and a production rate of a chemical.

The cleaning time for intermittent scrubbing cleaning is 5 seconds/time to 1 hour/time, more preferably 10 seconds/time to 600 seconds/time. Scrubbing cleaning time within one hour can prevent occurrence of problems such as damage or drying of a filtration membrane and an increase in the operation cost. Scrubbing cleaning time of 5 seconds or more can achieve a sufficient cleaning effect and at the same time can prevent contamination of unwanted microorganisms in the fermentor because a pressure reduction therein can be suppressed. It is to be noted that the gas linear velocity can be regulated depending on the scrubbing cleaning time.

3-5. Second Gas Supply Step

The production method of a chemical may further have a step of supplying a gas to the fermentor in addition to the step (d). In the constitution of FIG. 1, this step of supplying a gas to the fermentor 1 can be conducted using the fermentor gas supply apparatus 21 and the stirring apparatus 4.

In particular, when scrubbing cleaning is conducted intermittently, a gas supply amount necessary for the growth of microorganisms can be maintained by supplying a gas to the fermentor while terminating the gas supply for scrubbing. Namely, when scrubbing is conducted intermittently in the continuous fermentation apparatus 100, the control apparatus 28 works so that a gas supply rate to the fermentor 1 by another mechanism such as the fermentor gas supply apparatus 21 and the stirrer 4 at the time of terminating scrubbing increases over a gas supply rate to the fermentor 1 by the another mechanism at the time of conducting scrubbing. The extent of the increase in the supply rate can be changed, depending on the fermentation conditions and the like.

3-6. Backwashing

The production method of a chemical further has a backwashing step of the separation membrane of the separation membrane module. In the constitution of FIG. 1, the cleaning pipe 84 is connected to the secondary side of the separation membrane module 2 so that a cleaning liquid can be introduced into the separation membrane module 2 by a cleaning pump 13.

When backwashing is conducted, filtration is stopped to prevent a cleaning liquid from entering a filtrate tank in which a filtrate is retained. In other words, the filtration valve 12 is closed and at the same time, the filtration pump 11 is terminated. Under this state, the cleaning valve 14 is opened and the cleaning pump 13 starts operation, by which backwashing is conducted.

When backwashing is terminated, the cleaning valve 14 is closed and the cleaning pump 13 is terminated. Under this state, the filtration valve 12 is opened and the filtration pump 11 starts operation, by which filtration is conducted.

Such a control can be conducted by the control apparatus 28. The continuous fermentation apparatus 100 may be equipped with a measuring device such as timer, which is not illustrated, to determine the starting time or terminating time of backwashing.

Examples of the cleaning liquid to be used for backwashing include liquids having no adverse effect on fermentation and at the same time capable of cleaning the separation membrane such as water, the filtrate, the fermentation medium, some components to be added to the fermentation medium, and an aqueous solution of hydrochloric acid, sulfuric acid, nitric acid, sodium hydroxide, calcium hydroxide, or sodium hypochlorite, and mixtures thereof.

4. Chemical

The chemical available by the production method described herein is a substance produced by cells in a culture medium. Examples of the chemical include substances mass produced in the fermentation industry such as alcohols, organic acids, diamines, amino acids, and nucleic acids. The production method can also be applied to the production of a substance such as enzymes, antibiotics, and recombinant proteins.

Examples of the alcohols include ethanol, 1,3-butanediol, 1,4-butanediol, and glycerol.

Examples of the organic acids include acetic acid, lactic acid, pyruvic acid, succinic acid, malic acid, itaconic acid, amino acid, and citric acid. Examples of the diamines include cadaverine, while those of the nucleic acids include inosine, guanosine, and citidine.

Examples of the amino acids include L-threonine, L-lysine, L-glutamic acid, L-tryptophan, L-isoleucine, L-glutamine, L-arginine, L-alanine, L-histidine, L-proline, L-phenylalanine, L-aspartic acid, L-tyrosine, L-methionine, L-serine, L-valine, and L-leucine. Of these, L-threonine, L-lysine, and L-glutamic acid are particularly preferred.

EXAMPLES

Our methods will hereinafter be described more specifically by Examples. It should however be born in mind that our methods are not limited to or by these Examples. The schematic constitution of a continuous fermentation apparatus used in the following Examples is similar to that of FIG. 1 except for the constitution relating to scrubbing cleaning. In the following Examples, L-threonine and L-lysine were produced as a chemical through continuous fermentation.

A. Measuring Method of L-Threonine Concentration

The concentration of L-threonine contained in a culture medium was measured using the following method. After 25 μL of a culture medium containing L-threonine to be measured was weighed, 150 μl of $NaHCO_3$ (75 mM) and, as an internal standard, 25 μl of L-methionine (2 g/L) were added. To the resulting solution were added 900 μl of ethanol and 150 μl of 0.2M dinitrofluorobenzene (DFNB), followed by mixing. The resulting mixture was allowed to stand at 37° C. for one hour and then, subjected to HPLC analysis under the following conditions:

Column: CAPCELLPAK C18 TYPE SG120 (product of Shiseido)

Mobile phase: 0.1% (w/v) $H_3PO_4$:acetonitrile=7:3 (flow rate: 1.2 mL/min)

Detection method: UV (360 nm)

Temperature: 23° C.

A calibration curve was drawn by conducting analysis while using L-threonine having a known concentration as a standard preparation and plotting the L-threonine concentration on the abscissa and an (L-threonine area)/(L-methionine (internal standard) area) ratio on the ordinate.

B. Measuring Method of L-Lysine Concentration

The concentration of L-lysine contained in a culture medium was measured using the following method. After 25 μL of a culture medium containing L-lysine to be measured was weighed, 400 μL of $NaHCO_3$ (75 mM) and, as an internal standard, 25 μL of 1,4-butanediol (2 g/L) were added. To the resulting solution was added 150 μl of 0.2 MDNFB and the resulting mixture was reacted at 37° C. for one hour.

The reaction mixture (50 μl) was dissolved in 1 mL of acetonitrile and 10 μl of a supernatant obtained by centrifuging the resulting solution at 10,000 rpm for 5 minutes was analyzed under the following conditions by using HPLC:
Column: CAPCELLPAK C18 TYPE SG120 (product of Shiseido)
Mobile phase: (0.1% (w/w) aqueous solution of phosphoric acid):acetonetrile=45:55 (flow rate: 1 mL/min)
Detection method: UV (360 nm)
Temperature: 23° C.

A calibration curve was drawn by conducting analysis while using L-lysine having a known concentration as a standard preparation and plotting the L-lysine concentration on the abscissa and an (L-lysine area)/(1,4-butanediol (internal standard area) ratio on the ordinate.

C. Measuring Method of L-Lactic Acid Concentration

The concentration of L-lactic acid contained in a culture medium was measured using the following method. It was confirmed by weighing 100 µL of a culture medium containing L-lactic acid and measuring an amount of lactic acid under the following conditions by using HPLC:
Column: Shim-Pack SPR-H (product of Shimadzu)
Mobile phase: 5 mM p-toluenesulfonic acid (flow rate: 0.8 mL/min)
Reaction liquid: 5 mM p-toluenesulfonic acid, 20 mM Bis-Tris, 0.1 mM
EDTA.2Na (flow rate: 0.8 mL/min)
Detection method: electroconductivity
Temperature: 45° C.

A calibration curve was drawn by conducting analysis while using L-lactic acid having a known concentration as a standard preparation and plotting the concentration of L-lactic acid on the abscissa and a detection peak area on the ordinate.

D. Measuring Method of Glucose Concentration

"Glucose test Wako C" (trade mark) (product of Wako Pure Chemical Industries) was used for measuring the concentration of glucose.

The concentration of microorganisms was determined by measuring the absorption at OD 600 nm of an appropriately diluted fermentation liquid.

E. Manufacture of Hollow Fiber Module

A polyvinylidene fluoride hollow fiber pressured type module "HFS1020" manufactured by Toray Industries was disassembled and only a portion not fixed with an adhesive was cut out. The polyvinylidene fluoride hollow fiber membrane thus cut out was housed in a case to prepare a hollow fiber membrane module as a separation membrane module. The case used was that made of a polycarbonate resin. The hollow fiber membrane module thus prepared had a capacity of 0.02 L and an effective filtration area of 200 cm². In all of Examples and Comparative Examples, a module of the same type was employed.

F. Preparation of Gene Recombinant Strain to be Used for Preparation of L-Lysine Through Continuous Fermentation As a microorganism having an L-lysine production capacity, a homoserine dehydrogenase (HOM) gene disrupted strain of *Corynebacterium glutamicum* ATCC13032 (which will hereinafter be abbreviated as "ATCC13032 strain") was prepared. More specifically, genetic modification was conducted according to the method described in JP-A-2008-212138. The strain thus obtained is called *Corynebacterium glutamicum* delta-HOM strain (which will hereinafter be abbreviated as "delta-HOM strain"). Using the delta-HOM strain, continuous fermentation of L-lysine was conducted as described later.

G. Preparation of Gene Recombinant Strain to be Used for the Preparation of L-Lactic Acid Through Continuous Fermentation A yeast having a *Xenopus laevis*-derived ldh gene introduced into the PDC1 locus, the SED1 locus, and the TDH3 locus was prepared. The ldh gene has a base sequence described in SEQ ID NO: 1. Cloning of the *Xenopus laevis*-derived ldh gene was conducted using PCR. In PCR, a phagemid DNA was used as a template which was prepared using a cDNA library (product of STRATAGENE) derived from the kidney of *Xenopus laevis* according to the protocol attached thereto.

In PCR, KOD-Plus polymerase (product of Toyobo) was used. As a reaction buffer, dNTP mix, and the like, those attached to it were used.

A PCR reaction solution was 50 µl per sample and it was prepared to contain 50 ng/sample of the phagemid DNA prepared according to the manufacturer's protocol, 50 pmol/sample of primers and 1 Unit/sample of KOD-Plus polymerase. The reaction solution was thermally denatured (thermal denaturation) by using a PCR amplification device iCycler (product of BIO-RAD) at 94° C. for 5 minutes, followed by 30 cycles of treatment including heat denaturation at 94° C. for 30 seconds, annealing of the primer at 55° C. for 30 seconds, and extension of the complementary strand at 68° C. for 1 minute. The reaction solution was then cooled to 4° C. The primers (SEQ ID NOS: 2 and 3) for gene amplification were prepared so that the SalI-recognition sequence and the NotI recognition sequence were added to the 5'-end and the 3'-end, respectively.

The PCR amplification fragment was purified, phosphorylated, at the ends thereof, with T4 polynucleotide Kinase (product of TAKARA BIO INC.), and then ligated to a pUC118 vector (which had been digested with a restriction enzyme HincII and the digested ends had been subjected to dephosphorylation treatment). The ligation was conducted using DNA Ligation Kit Ver.2 (product of TAKARA BIO INC.). Competent cells of *Escherichia coli* DH5α (product of TAKARA BIO INC.) were transformed with the ligation solution, seeded on an LB plate containing 50 µg/mL of an antibiotic ampicillin, and cultured overnight. Plasmid DNAs were collected from the colonies thus grown by using a miniprep method and digested with restriction enzymes SalI and NotI. Then, a plasmid having the *Xenopus laevis*-derived ldh gene inserted therein was selected. The above-mentioned series of operation was entirely carried out according to the manufacturer's protocol.

The pUC118 vector having the *Xenopus laevis*-derived ldh gene inserted therein was digested with restriction enzymes SalI and NotI and the DNA fragments were separated using 1% agarose gel electrophoresis. Then, the fragment containing the *Xenopus laevis*-derived ldh gene was purified according to a conventional method.

Figure 14:
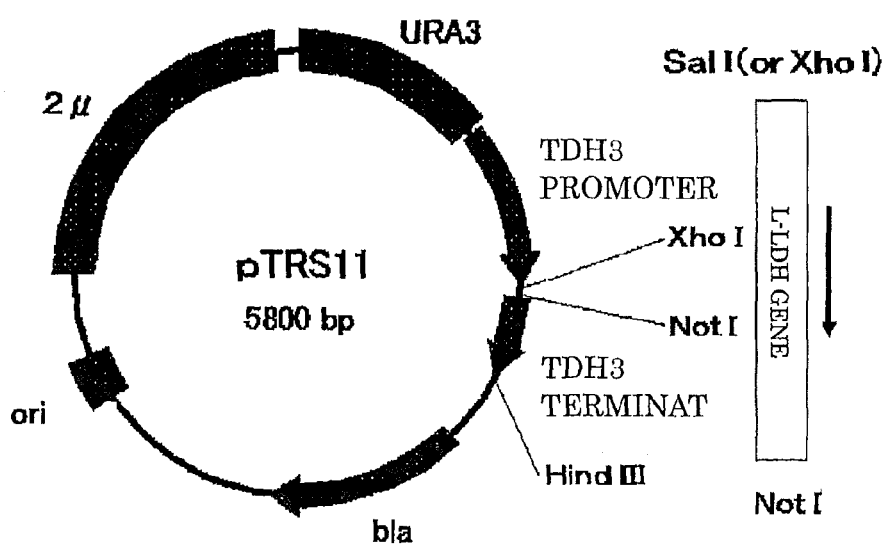
FIG. 14 is a sequence map of plasmid pTRS11.

The ldh-gene-containing fragment thus obtained was ligated to the XhoI/NotI-digestion site in the expression vector pTRS11 shown in FIG. 14. Plasmid DNA was recovered in a similar manner to that described above and digested with restriction enzymes XhoI and NotI to select an expression vector having the *Xenopus laevis*-derived ldh gene introduced therein. The expression vector having the *Xenopus laevis*-derived ldh gene introduced therein and prepared in such a manner will hereinafter be called "pTRS102."

Using this pTRS102 as an amplification template and oligonucleotides (SEQ ID NOS: 4 and 5) as a primer set, PCR was carried out to amplify a PCR fragment of 1.3 kb containing the *Xenopus laevis*-derived ldh gene and the TDH3 terminator sequence. Incidentally, SEQ ID NO: 4 was designed so that a sequence corresponding to 60 bp upstream of the initiation codon of the PDC1 gene was added.

Next, with plasmid pRS424 as an amplification template and oligonucleotides (SEQ ID NOS: 6 and 7) as a primer set, PCR was carried out to amplify a PCR fragment of 1.2 kb containing a TRP1 gene as a yeast selection marker. Incidentally, SEQ ID NO: 7 was designed so that a sequence corresponding to 60 bp downstream of the termination codon of the PDC1 gene was added.

The individual DNA fragments thus obtained were separated using 1% agarose gel electrophoresis and purified in a conventional manner. Using a mixture of the resulting 1.3 kb fragment and 1.2 kb fragment as an amplification template and oligonucleotides (SEQ ID NOS: 4 and 7) as a primer set, PCR was carried out. As a result, a PCR fragment of about 2.5 kb was amplified. In the resulting fragment, sequences corresponding to 60 bp upstream and downstream of the PDC1 gene were added to the 5'-end and 3'-end, respectively and the *Xenopus laevis*-derived ldh gene, TDH3 terminator, and TRP1 gene were linked to each other.

The resulting PCR fragment was separated using 1% agarose gel electrophoresis, purified in a conventional manner, transformed into a yeast *Saccharomyces cerevisiae* NBRC10505 strain, and cultured on a tryptophan-free medium. Thus, a transformant strain having the *Xenopus laevis*-derived ldh gene introduced at a site downstream of the PDC1 gene promoter on the chromosome was selected.

It was confirmed as described below that the transformant strain thus obtained was a yeast having the *Xenopus laevis*-derived ldh gene introduced into the downstream of the PDC1 gene promoter on the chromosome. First, a genomic DNA of the transformant strain was prepared using a genomic DNA extraction kit "Dr. GenTLE" (product of TAKARA BIO INC.). Using the resulting genomic DNA as an amplification template and oligonucleotides (SEQ ID NOS: 7 and 8) as a primer set, PCR was conducted to obtain an amplified DNA fragment of about 2.8 kb. As a result, it was confirmed that the transformant strain thus obtained was the above-mentioned yeast. When a non-transformant strain is used, an amplified DNA fragment of about 2.1 kb can be obtained using the above-mentioned PCR.

The transformant strain having the *Xenopus laevis*-derived ldh gene introduced at a site downstream of the PDC1 gene promoter on the chromosome will hereinafter be called "B2 strain." The upstream and downstream sequences of the PDC1 gene can be obtained from *Saccharomyces* Genome Database (URL: http://ww.yeastgenome.org/).

Then, the ldh gene described in SEQ ID NO: 1 was introduced into the SED1 gene locus of this B2 strain. Described specifically, using pTRS102 described above as an amplification template and oligonucleotides (SEQ ID NOS: 5 and 9) as a primer set, PCR was carried out to amplify a PCR fragment of 1.3 kb containing the *Xenopus laevis*-derived ldh gene and the TDH3 terminator sequence. The SEQ ID NO: 9 was designed so that the sequence corresponding to 60 bp upstream of the initiation codon of the SED1 gene was added.

Next, using plasmid pRS423 as an amplification template and oligonucleotides (SEQ ID NOS: 6 and 10) as a primer set, PCR was carried out to amplify a PCR fragment of about 1.3 kb containing an HIS3 gene, that is, a yeast selection marker. The SEQ ID NO: 10 was designed so that the sequence corresponding to 60 bp downstream of the termination codon of the SED1 gene was added.

The DNA fragments thus obtained were separated using 1% agarose gel electrophoresis and purified in a conventional manner. Using a mixture of the two fragments of about 1.3 kb thus obtained as an amplification template and oligonucleotides (SEQ ID NOS: 9 and 10) as a primer set, PCR was carried out to obtain a PCR fragment of about 2.6 kb in which sequences corresponding to 60 bp upstream and downstream of the SED1 gene were added to the 5'-end and 3'-end, respectively and the *Xenopus laevis*-derived ldh gene, the TDH3 terminator, and the HIS3 gene were linked to each other.

The PCR fragment was separated using 1% agarose gel electrophoresis, purified in a conventional manner, transformed into the B2 strain, and cultured on a histidine-free medium. Thus, a transformant strain having the *Xenopus laevis*-derived ldh gene introduced at a site downstream of the SED1 gene promoter on the chromosome was selected.

It was confirmed as described below that the transformant strain thus obtained was a yeast having the *Xenopus laevis*-derived ldh gene introduced at a site downstream of the SED1 gene promoter on the chromosome. First, the genomic DNA of the transformant strain was prepared using a genomic DNA extraction kit "Dr. GenTLE" (product of TAKARA BIO INC). Using the resulting genomic DNA as an amplification template and oligonucleotides (SEQ ID NOS: 11 and 12) as a primer set, PCR was conducted to obtain an amplified DNA fragment of about 2.9 kb. As a result, it was confirmed that the transformant strain thus obtained was a yeast having the above-mentioned gene introduced therein. When a non-transformed strain is used, an amplified DNA fragment of about 1.4 kb is obtained using the above-mentioned PCR. The transformant strain having the *Xenopus laevis*-derived ldh gene introduced at a site downstream of the SED1 gene promoter on the chromosome will hereinafter be called "SUO14-I strain."

Next, the ldh gene described in SEQ ID NO: 1 was introduced into the TDH3 locus of SUO14-1. The introduction into the TDH3 locus was conducted by preparing a plasmid by replacing the TDH3 terminator of pTRS102 with the ADH1 terminator.

First, a genomic DNA was prepared from the NBRC10505 strain by using a genomic DNA extraction kit "Dr. GenTLE" (product of TAKARA BIO INC.). Using the extracted genomic DNA as a template and oligonucleotides (SEQ ID NOS: 13 and 14) as a primer set, PCR was conducted, by which a PCR fragment containing the ADH1 promoter was amplified. To the 5'-end side of SEQ ID NO: 13 was added a NotI recognition sequence and to the 3'-end side of SEQ ID NO: 14 was added a HindIII recognition sequence.

The PCR amplified fragment was purified, phosphorylated, at the end thereof, with T4 polynucleotide Kinase (product of TAKARA BIO INC.), and then, ligated to a pUC118 vector (which had been digested with a restriction enzyme HincII and the digested ends had been subjected to dephosphorylation treatment). The ligation solution was transformed into *E. coli* DH5α Competent Cells (product of TAKARA BIO INC.), followed by seeding and culturing on an LB plate containing 50 μg/mL of ampicillin, that is, an antibiotic. From the colonies thus grown, a plasmid DNA was recovered by a miniprep procedure and digested with restriction enzymes NotI and HindIII to select a plasmid having an ADH1 terminator inserted therein. The plasmid thus prepared will be called "pUC118-ADH1t."

Next, pUC118-ADH1t was digested with restriction enzymes NotI and HindIII; the DNA fragment was separated using 1% agarose gel electrophoresis; and a fragment containing the ADH1 terminator was purified in a conventional manner. The resulting fragment containing the ADH1 terminator was ligated to the NotI/HindIII digestion site in pTRS102. A plasmid DNA was recovered in a similar manner to that described above, followed by digestion with restriction enzymes NotI and HindIII to select a plasmid having the ADH1 terminator instead of the TDH3 terminator. The plasmid thus prepared will hereinafter be called "pTRS150."

Using this pTRS150 as a template and oligonucleotides (SEQ ID NOS: 15 and 16) as a primer set, PCR was conducted. By this PCR, a PCR fragment of 1.3 kb containing a frog-derived L-ldh gene and the ADH1 terminator sequence was amplified. The primer of SEQ ID NO: 16 was designed so that the sequence corresponding to 60 bp upstream of the initiation codon of the TDH3 gene was added.

Next, with the plasmid pRS426 as an amplification template and oligonucleotides (SEQ ID NOS: 17 and 18) as a primer set, PCR was conducted. By this PCR, a PCR fragment of 1.2 kb containing a URA3 gene, that is, a yeast selection marker, was amplified. The primer of SEQ ID NO: 18 was designed so that the sequence corresponding to 60 bp downstream of the termination codon of the TDH3 gene was added.

These PCR fragments thus obtained were separated using 1% agarose gel electrophoresis and purified in a conventional manner. Using a mixture of the resulting 1.3 kb fragment and 1.2 kb fragment as an amplification template and oligonucleotides (SEQ ID NOS: 16 and 18) as a primer set, PCR was carried out. In such a manner, a PCR fragment of about 2.5 kb in which the flog-derived L-ldh gene, the ADH1 terminator, and the URA gene had been linked to each other was amplified.

The PCR fragment was separated using 1% agarose gel electrophoresis and purified in a conventional manner. Then, the fragment thus obtained was transformed into the SUO14-I strain, followed by culturing on a uracil-free medium. In such a manner, a transformant strain having a chromosome in which a frog-derived L-ldh gene had been introduced at a site downstream of the TDH3 gene promoter was selected.

It was confirmed as described below that the transformant strain thus obtained was a yeast in which the frog-derived L-ldh gene had been introduced at a site downstream of the TDH3 gene promoter on the chromosome. First, the genomic DNA of the transformant strain was prepared using a genomic DNA extraction kit "Dr. GenTLE" (product of TAKARA BIO INC). Using the resulting genomic DNA as an amplification template and oligonucleotides (SEQ ID NOS: 19 and 20) as a primer set, PCR was conducted. When an amplified DNA fragment of about 2.8 kb is obtained by the above PCR, the transformant strain is the above-described yeast. When a non-transformed strain is used, an amplified DNA fragment of about 2.1 kb is obtained using the above-mentioned PCR. The transformant strain having the frog-derived L-ldh gene introduced at a site downstream of the TDH3 gene promoter on the chromosome will hereinafter be called "SUO14-II strain."

Next, a diploid cell was obtained by joining a yeast SW015 strain having a temperature-sensitive mutation in a pdc5 gene and the SUO14-II strain obtained above. The SWO15 strain is described in WO2007/097260. Asci of the diploid cell were formed on an ascus formation medium. The asci were each dissected by a micromanipulator to obtain monoploid cells, respectively.

The auxotrophy of the monoploid cells thus obtained was examined. From the acquired monoploid cells, selected were strains exhibiting a MATa mating type and MATα mating type were selected from the strains having the *Xenopus-Laevis* derived ldh gene inserted into the pdc1 locus, sed1 locus, and tdh3 locus and having a temperature-sensitive mutation in a pdc5 gene (incapable of growing at 34° C.). Among the yeast strains thus obtained, the strain exhibiting a MATa mating type and the strain exhibiting a MATα mating type will hereinafter be called "SU014-8A strain" and "SU014-3B strain," respectively.

The SU014-8A strain and SU014-3B strain thus obtained were joined to obtain an auxotrophic diploid strain having auxotrophy. The resulting strain will be called "SU014."

H. Production of L-Threonine Through Continuous Fermentation

Comparative Example 1

Continuous fermentation of L-threonine was conducted by operating the continuous fermentation apparatus shown in FIG. 1. As the separation membrane, the hollow fiber membrane manufactured described above was used. Following are operation conditions of continuous fermentation of L-threonine common to the following Examples and Comparative Examples.

Common Conditions
  Microorganism: *Providencia rettgeri* SGR588-77 strain (FERMP-10528)
  Medium: L-threonine fermentation medium (Table 1)
  Volume of fermentation liquid: 3.0 (L)
  Hollow fiber membrane MD volume: 0.02 (L)
  Temperature: 37 (° C.)
  Fermentor stirring rate: 350 (rpm)
  Sterilization: a fermentor including a hollow fiber membrane module and a medium used are all subjected to high-pressure (2 atmospheric pressures) steam sterilization in an autoclave at 121° C. for 20 min.
  pH Adjustment: adjusted to pH 7 with a 28% aqueous ammonia solution
  Circulating pump flow rate: 3 L/min
  Filtration rate: 170 ml/h (fixed)

TABLE 1

L-threonine fermentation medium for *Providencia rettgeri*

| Component | Amount | Unit |
| --- | --- | --- |
| Glucose | 60 | g/L |
| Ammonium sulfate | 5 | g/L |
| Potassium dihydrogen phosphate | 1 | g/L |
| Magnesium sulfate heptahydrate | 0.4 | g/L |
| Iron sulfate heptahydrate | 2 | ppm |
| Manganese sulfate pentahydrate | 2 | ppm |
| L-Isoleucine | 10 | g/L |

Conditions specific to this Comparative Example (altered conditions) are as follows.

Altered Conditions:
  Amount of gas supplied from module scrubbing gas supply apparatus (16): none
  Amount of gas supplied from pipe scrubbing gas supply apparatus (18): none
  Amount of gas supplied from upstream-of-pump pipe scrubbing gas supply apparatus (20): none
  Gas linear velocity: 0 cm/s
  Amount of gas supplied from fermentor gas supply apparatus (21): 75 ml/min.

The conditions such as a medium and the like described below are common to Examples and Comparative Examples. With regards to fermentation feedstocks, glucose was used as a carbon source irrespective of the intended chemical substance. As a nitrogen source and inorganic salt, substances described below were used, respectively.

First, a *Providencia rettgeri* SGR588-77 strain scraped off from an agar medium was inoculated in a 500-ml conical flask charged with 100 ml of a glucose-bouillon medium (1% glucose, 3% bouillon (product of Nissui Co., Ltd.)) and it was cultured at 37° C. under stirring at 140 rpm (this means that preculturing was conducted). The preculture was inoculated in a continuous fermentation apparatus charged with 3 L of an L-threonine fermentation medium (Table 1) and it was cultured for 24 hours. Then, continuous culture was conducted by continuously supplying the L-threonine fermentation medium while controlling the supply amount of the medium so that the culture medium amount in the fermentor became constant. Thus, L-threonine was produced through continuous fermentation.

The L-threonine concentration and the residual glucose concentration contained in the filtrate were measured using the methods shown in [A] and [D], respectively.

Figure 2:
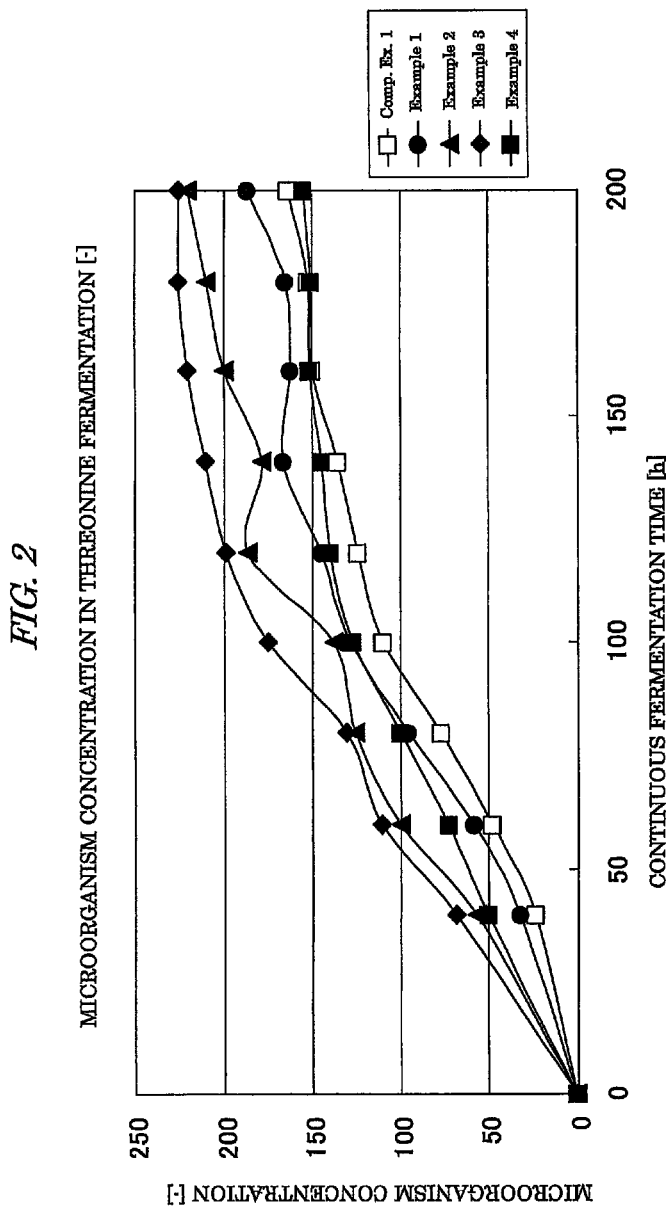
FIG. 2 is a chart showing a change in microorganism concentration in Comparative Example 1 and Examples 1 to 4.
Figure 3:
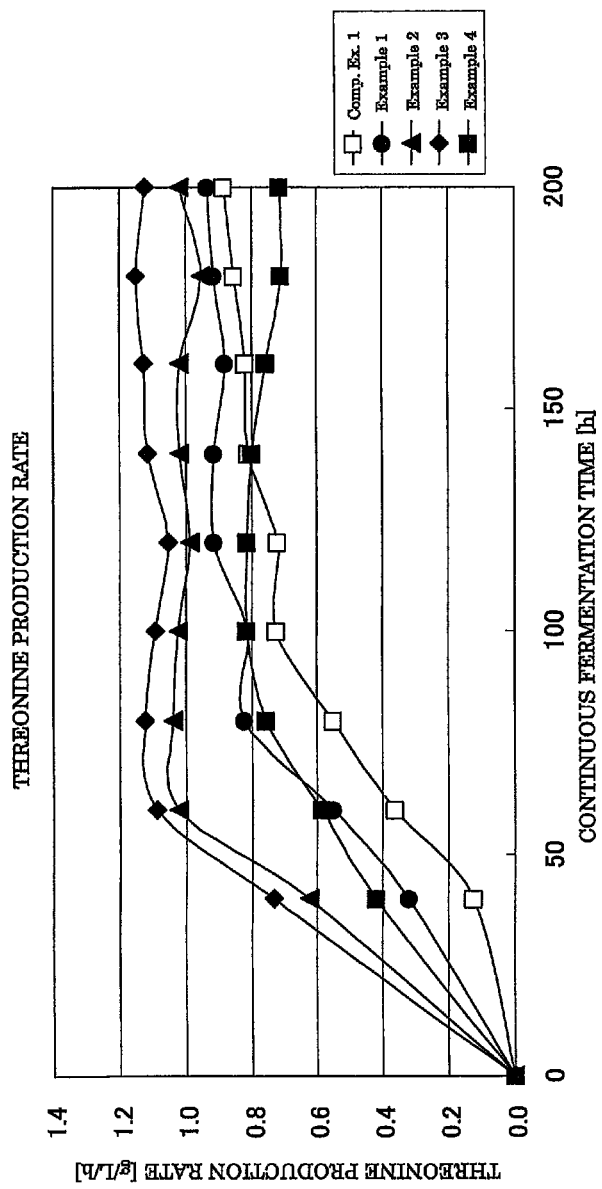
FIG. 3 is a chart showing a change in production rate in Comparative Example 1 and Examples 1 to 4.
Figure 4:
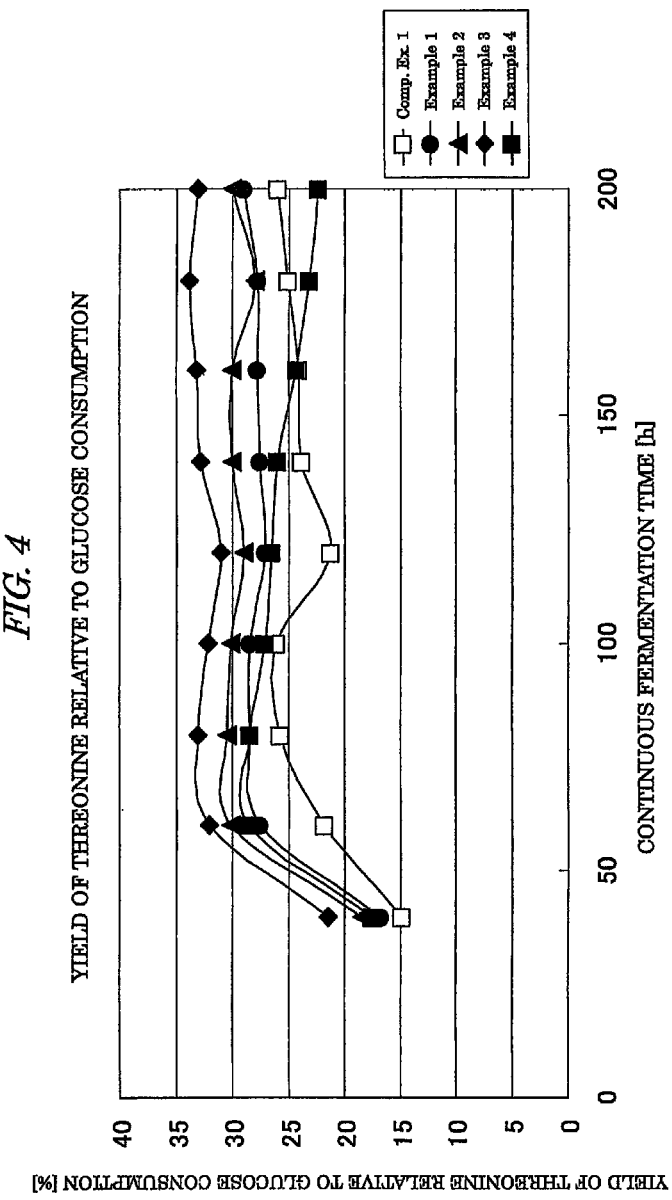
FIG. 4 is a chart showing a change in yield relative to glucose consumption in Comparative Example 1 and Examples 1 to 4.
Figure 5:
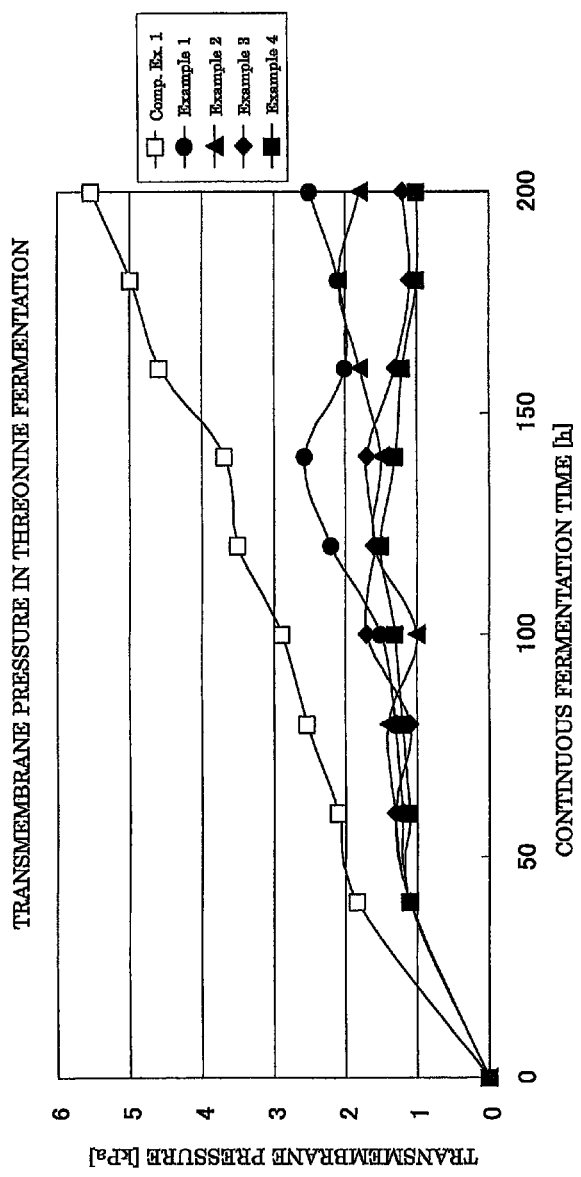
FIG. 5 is a chart showing a change in transmembrane pressure difference in Comparative Example 1 and Examples 1 to 4.

Changes in microorganism concentration (–) in the fermentation liquid in the present Comparative Example are shown in FIG. 2; changes in the L-threonine production rate (g/L/h) are shown in FIG. 3; and changes in yield (%) relative to glucose consumption are shown in FIG. 4. In addition, changes in transmembrane pressure difference (kPa) are shown in FIG. 5.

Comparative Example 2

Under conditions similar to those employed in Comparative Example 1 except for the following conditions, continuous fermentation was conducted:
  Amount of gas supplied from module scrubbing gas supply apparatus (16): none
  Amount of gas supplied from pipe scrubbing gas supply apparatus (18): 2500 ml/min
  Amount of gas supplied from upstream-of-pump pipe scrubbing gas supply apparatus (20): none
  Gas linear velocity: 88.5 cm/s
  Amount of gas supplied from fermentor gas supply apparatus (21): 75 ml/min.
The gas linear velocity was measured using the flow meter 93.

In this Comparative Example, severe foaming of the fermentation liquid in the fermentor occurred. The resulting foams reached the exhaust port present in the upper portion of the fermentor, come into contact with the outside air, and caused contamination, making it impossible to conduct continuous fermentation.

Example 1

Continuous fermentation was conducted under conditions similar to those employed in Comparative Example 1 except for the following conditions:
  Amount of gas supplied from module scrubbing gas supply apparatus (16): 5 ml/min
  Amount of gas supplied from pipe scrubbing gas supply apparatus (18): none
  Amount of gas supplied from upstream-of-pump pipe scrubbing gas supply apparatus (20): none
  Gas linear velocity: 0.18 cm/s
  Amount of gas supplied from fermentor gas supply apparatus (21): 75 ml/min.

Changes in microorganism concentration (–) in the fermentation liquid in this Example are shown in FIG. 2; changes in L-threonine production rate (g/L/h) are shown in FIG. 3; and changes in yield (%) relative to glucose consumption are shown in FIG. 4. In addition, changes in transmembrane pressure difference (kPa) are shown in FIG. 5.

Compared with Comparative Example 1, a rise of the L-threonine production rate is improved and in addition, the L-threonine production rate and the yield relative to glucose consumption are improved. Moreover, an increasing rate of the transmembrane pressure difference is made smaller than that of Comparative Example 1 and the transmembrane pressure difference changes at low levels. Appearance of a membrane cleaning effect has therefore been confirmed. Cleaning of a membrane surface by using such a simple and easy method makes it possible to enhance the productivity of a chemical through continuous fermentation while keeping the filtration property of the separation membrane.

Example 2

Under conditions similar to those employed in Comparative Example 1 except for the following conditions, continuous fermentation was conducted:
  Amount of gas supplied from module scrubbing gas supply apparatus (16): none
  Amount of gas supplied from pipe scrubbing gas supply apparatus (18): 300 ml/min
  Amount of gas supplied from upstream-of-pump pipe scrubbing gas supply apparatus (20): none
  Gas linear velocity: 10.4 cm/s
  Amount of gas supplied from fermentor gas supply apparatus (21): 75 ml/min.

Changes in microorganism concentration (–) in the fermentation liquid in this Example are shown in FIG. 2; changes in L-threonine production rate (g/L/h) are shown in FIG. 3; and changes in yield (%) relative to glucose consumption are shown in FIG. 4. In addition, changes in transmembrane pressure difference (kPa) are shown in FIG. 5.

Compared with Comparative Example 1 and Example 1, a rise of the L-threonine production rate is improved further and in addition, the L-threonine production rate and the yield relative to glucose consumption are improved. An increasing rate of the transmembrane pressure difference is made smaller than that of Comparative Example 1 so that the transmembrane pressure difference changes at low levels. Appearance of a membrane cleaning effect has therefore been confirmed.

Example 3

Under conditions similar to those employed in Comparative Example 1 except for the following conditions, continuous fermentation was conducted:
  Amount of gas supplied from module scrubbing gas supply apparatus (16): none
  Amount of gas supplied from pipe scrubbing gas supply apparatus (18): none
  Amount of gas supplied from upstream-of-pump pipe scrubbing gas supply apparatus (20): 500 ml/min
  Gas linear velocity: 17.4 cm/s
  Amount of gas supplied from fermentor gas supply apparatus (21): 75 ml/min.

Changes in microorganism concentration (–) in the fermentation liquid in this Example are shown in FIG. 2; changes in L-threonine production rate (g/L/h) are shown in FIG. 3; and changes in yield (%) relative to glucose consumption are shown in FIG. 4. In addition, changes in transmembrane pressure difference (kPa) are shown in FIG. 5.

Compared with Comparative Example 1, Example 1, and Example 2, a rise of the L-threonine production rate is improved further and in addition, the L-threonine production rate and the yield relative to glucose consumption are improved. An increasing rate of the transmembrane pressure difference is made smaller than that of Comparative Example 1 so that the transmembrane pressure difference changes at low levels. Appearance of a membrane cleaning effect has therefore been confirmed. Thus, it has been confirmed that scrubbing is effective irrespective of the supply position thereof.

Example 4

Under conditions similar to those employed in Comparative Example 1 except for the following conditions, continuous fermentation was conducted:
  Amount of gas supplied from module scrubbing gas supply apparatus (16): none
  Amount of gas supplied from pipe scrubbing gas supply apparatus (18): 2000 ml/min
  Amount of gas supplied from upstream-of-pump pipe scrubbing gas supply apparatus (20): none
  Gas linear velocity: 70 cm/s
  Amount of gas supplied from fermentor gas supply apparatus (21): 75 ml/min.

Changes in microorganism concentration (-) in the fermentation liquid in this Example are shown in FIG. 2; changes in L-threonine production rate (g/L/h) are shown in FIG. 3; and changes in yield (%) relative to glucose consumption are shown in FIG. 4. In addition, changes in transmembrane pressure difference (kPa) are shown in FIG. 5.

Compared with Comparative Example 1, a rise of the L-threonine production rate is improved further and in addition, the L-threonine production rate and the yield relative to glucose consumption are improved. Moreover, an increasing rate of the transmembrane pressure difference is made smaller than that of Comparative Example 1 so that the transmembrane pressure difference changes at low levels. Appearance of a membrane cleaning effect has therefore been confirmed. It has been confirmed that in the present Example, compared with Comparative Example 2, continuous fermentation can be conducted for a long period of time without causing much foam and contamination.

I. Production of L-Lysine Through Continuous Fermentation

Comparative Example 3

By using the continuous fermentation apparatus shown in FIG. 1, continuous fermentation of L-lysine was conducted. As the separation membrane, the hollow fiber membrane manufactured in [F] was used. The following are operation conditions for continuous fermentation of L-lysine common to Examples and Comparative Examples.

Common Conditions:
  Microorganism: *Corynebacterium glutamicum* delta-HOM strain
  Medium: L-lysine fermentation medium (Table 2)
  Volume of fermentation liquid: 3.0 (L)
  Hollow fiber membrane MD volume: 0.02 (L)
  Temperature: 30 (° C.)
  Fermentor stirring rate: 350 (rpm)
  Sterilization: fermentor including a hollow fiber membrane module and a medium used were all subjected to high-pressure (2 atmospheric pressures) steam sterilization in an autoclave at 121° C. for 20 minutes.
  pH Adjustment: adjusted to pH 7.3 with a 28% aqueous ammonia solution.
  Circulating pump flow rate: 3 L/min
  Filtration rate: 170 ml/h (fixed)

TABLE 2

L-lysine fermentation medium for *Corynebacterium*

| Component | Amount | Unit |
| --- | --- | --- |
| Glucose | 100 | g/L |
| Urea | 1 | g/L |
| Yeast extract | 5 | g/L |
| Dipotassium hydrogen phosphate | 2.5 | g/L |
| Magnesium sulfate heptahydrate | 175 | g/L |
| Calcium chloride dehydrate | 205 | g/L |
| Iron sulfate heptahydrate | 0.05 | g/L |
| Manganese sulfate pentahydrate | 13 | ppm |
| Copper sulfate pentahydrate | 6.3 | ppm |
| Zinc sulfate heptahydrate | 13 | ppm |
| Nickel chloride hexahydrate | 5 | ppm |
| Cobalt chloride hexahydrate | 1.3 | ppm |
| Molybdenum | 1.3 | ppm |
| β-alanine | 23 | ppm |
| Nicotinic acid | 14 | ppm |
| Biotin | 0.5 | ppm |
| Thiamine | 7 | ppm |

Altered Conditions:
  Amount of gas supplied from module scrubbing gas supply apparatus (16): none
  Amount of gas supplied from pipe scrubbing gas supply apparatus (18): none
  Amount of gas supplied from upstream-of-pump pipe scrubbing gas supply apparatus (20): none
  Gas linear velocity: 0 cm/s
  Amount of gas supplied from fermentor gas supply apparatus (21): 75 ml/min The delta-HOM strain scraped off from an agar medium was inoculated in a test tube charged with 5 ml of a BY medium (0.5% yeast extract, 0.7% meat extract, 1% peptone, and 0.3% sodium chloride), followed by shaking culture at 30° C. for 24 hours (pre-preculture). All the amount of the pre-preculture medium thus obtained was inoculated in a 500-mL conical flask charged with 50 mL of the medium shown in Table 2 and precultured at 30° C. The preculture medium thus obtained was inoculated in a continuous fermentation apparatus charged with 3 L of an L-lysine fermentation medium and cultured for 24 hours. Then, continuous culture was conducted by continuously supplying an L-lysine fermentation medium while controlling the supply amount of the culture medium in the fermentor to be constant. In such a manner, production of L-threonine through continuous fermentation was conducted.

The concentration of L-lysine produced in the filtrate and the residual glucose concentration were measured as needed by using the methods shown in [B] and [D], respectively.

Figure 6:
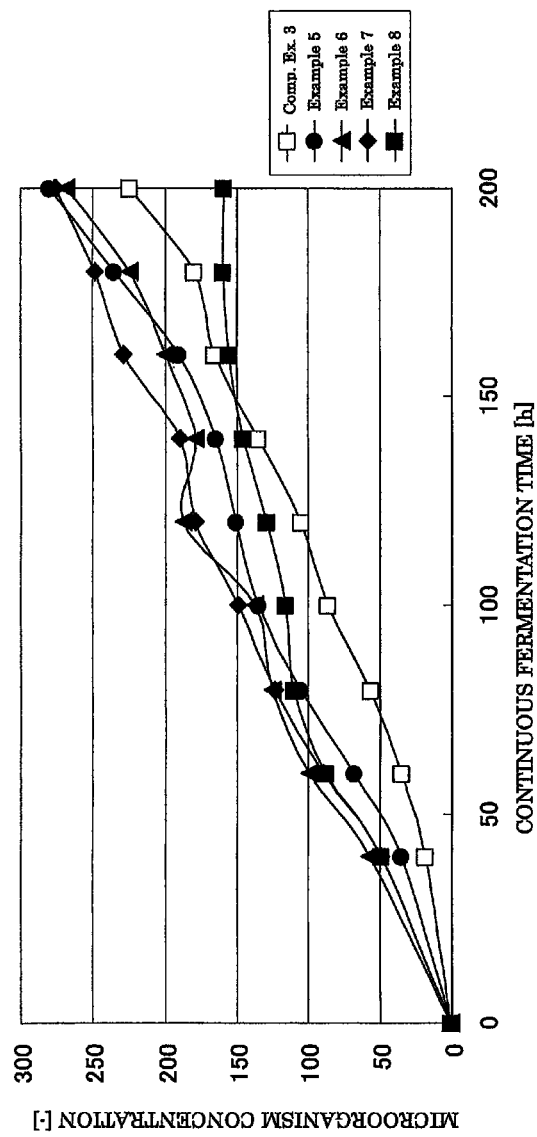
FIG. 6 is a chart showing a change in microorganism concentration in Comparative Example 3 and Examples 5 to 8.
Figure 7:
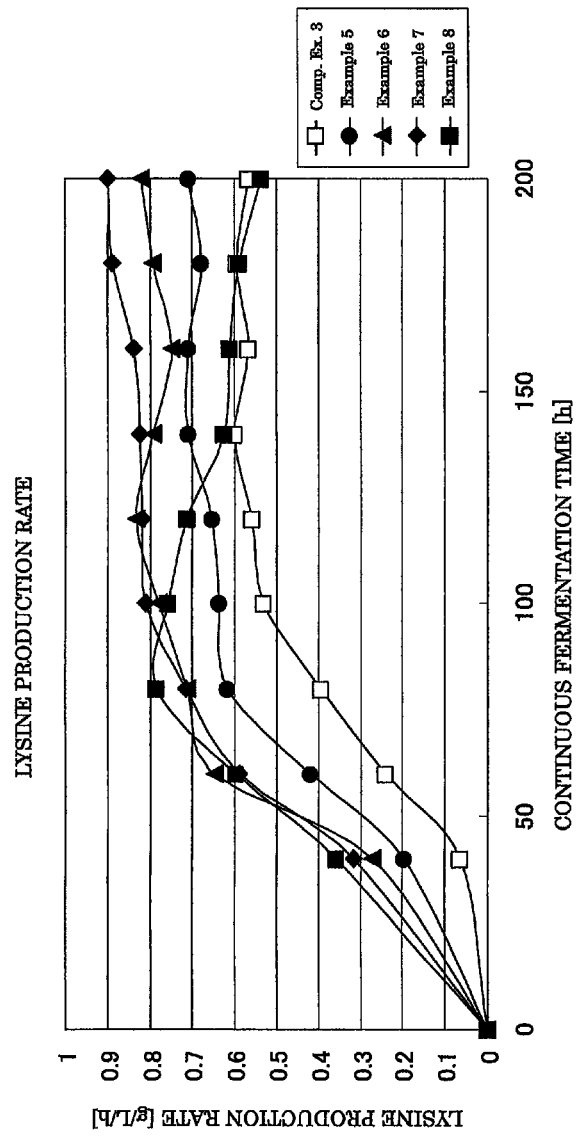
FIG. 7 is a chart showing a change in production rate in Comparative Example 3 and Examples 5 to 8.
Figure 8:
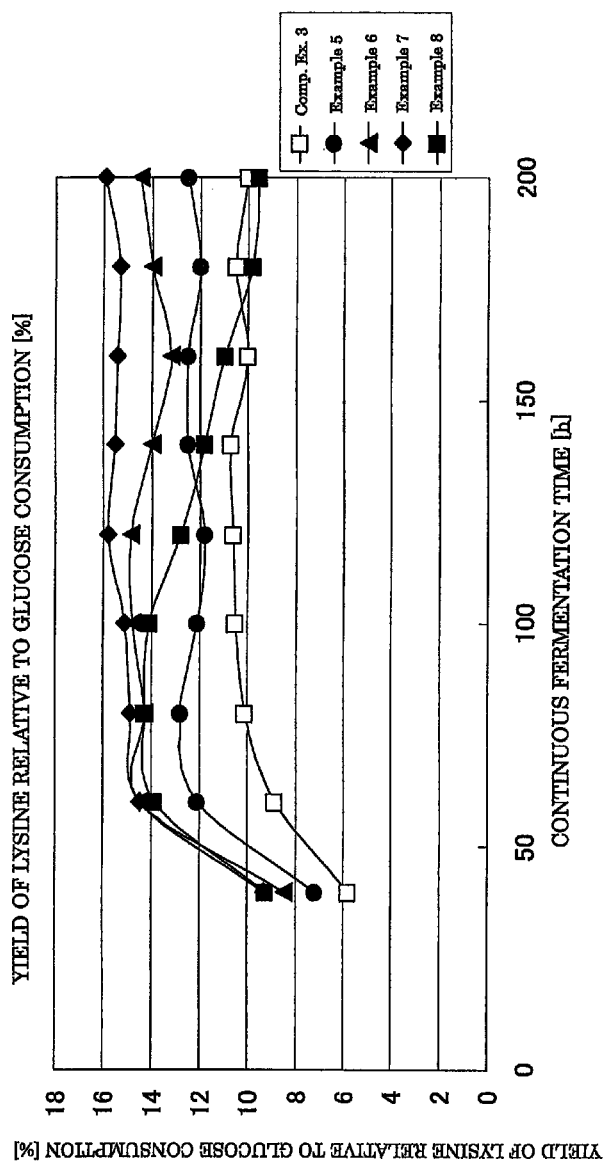
FIG. 8 is a chart showing a change in yield relative to glucose consumption in Comparative Example 3 and Examples 5 to 8.
Figure 9:
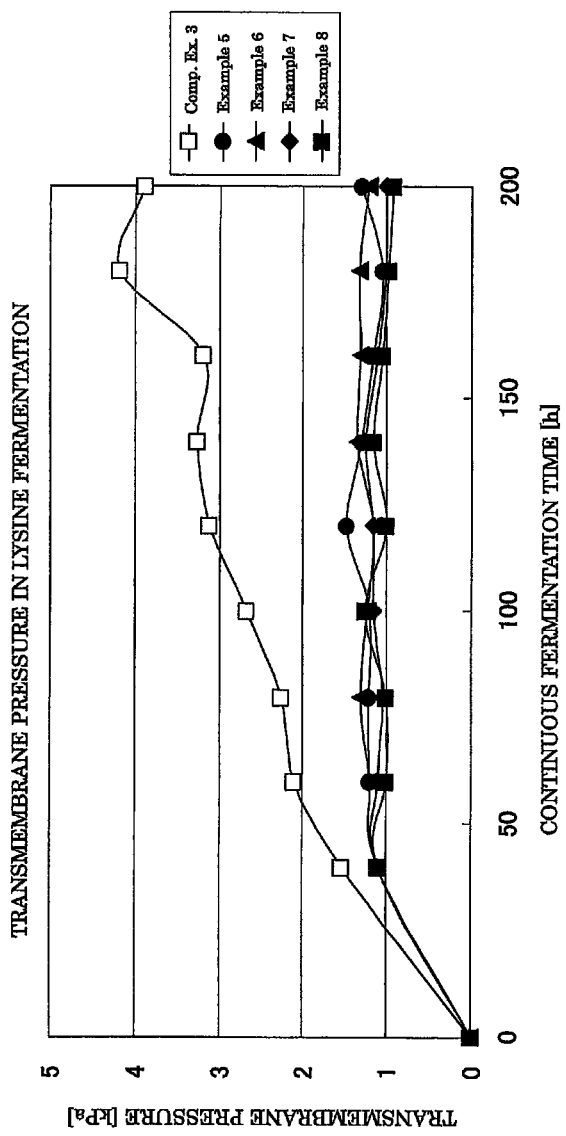
FIG. 9 is a chart showing a change in transmembrane pressure difference in Comparative Example 3 and Examples 5 to 8.

Changes in microorganism concentration (-) in the fermentation liquid in the present Comparative Example are shown in FIG. 6; changes in the L-lysine production rate (g/L/h) are shown in FIG. 7; and changes in yield (%) relative to glucose consumption are shown in FIG. 8. In addition, changes in transmembrane pressure difference (kPa) are shown in FIG. 9.

Comparative Example 4

Continuous fermentation was conducted under conditions similar to those employed in Comparative Example 3 except for the following conditions:
  Amount of gas supplied from module scrubbing gas supply apparatus (16): none
  Amount of gas supplied from pipe scrubbing gas supply apparatus (18): none Amount of gas supplied from upstream-of-pump pipe scrubbing gas supply apparatus (20): 2300 ml/min Gas linear velocity: 81.3 cm/s Amount of gas supplied from fermentor gas supply apparatus (21): 75 ml/min.

In this Comparative Example, the fermentation liquid in the fermentor severely foamed and the foam caused a malfunction of a level sensor for controlling a liquid surface. As a result, medium supply was stopped and the fermentation liquid was drained, making it impossible to conduct continuous fermentation.

Example 5

Continuous fermentation was conducted under conditions similar to those employed in Comparative Example 3 except for the following conditions:

Amount of gas supplied from module scrubbing gas supply apparatus (16): 800 ml/min Amount of gas supplied from pipe scrubbing gas supply apparatus (18): none Amount of gas supplied from upstream-of-pump pipe scrubbing gas supply apparatus (20): none Gas linear velocity: 27.8 cm/s Amount of gas supplied from fermentor gas supply apparatus (21): 75 ml/min.

Changes in microorganism concentration (–) in the fermentation liquid in this Example are shown in FIG. 6; changes in L-lysine production rate (g/L/h) are shown in FIG. 7; and changes in yield (%) relative to glucose consumption are shown in FIG. 8. In addition, changes in transmembrane pressure difference (kPa) are shown in FIG. 9.

Compared with Comparative Example 3, a rise of the L-lysine production rate is improved further and, in addition, the L-lysine production rate and the yield relative to glucose consumption are improved. Moreover, an increasing rate of the transmembrane pressure difference is made smaller than that of Comparative Example 3 so that the transmembrane pressure difference changes at low levels. Appearance of a membrane cleaning effect has therefore been confirmed. Cleaning of a membrane surface by using such a simple and easy method makes it possible to enhance the productivity of a chemical through continuous fermentation while keeping the filtration property of the separation membrane.

Example 6

Continuous fermentation was conducted under conditions similar to those employed in Comparative Example 3 except for the following conditions:

Amount of gas supplied from module scrubbing gas supply apparatus (16): none Amount of gas supplied from pipe scrubbing gas supply apparatus (18): 1000 ml/min Amount of gas supplied from upstream-of-pump pipe scrubbing gas supply apparatus (20): none Gas linear velocity: 34.7 cm/s Amount of gas supplied from fermentor gas supply apparatus (21): 75 ml/min.

Changes in microorganism concentration (–) in the fermentation liquid in this Example are shown in FIG. 6; changes in L-lysine production rate (g/L/h) are shown in FIG. 7; and changes in yield (%) relative to glucose consumption are shown in FIG. 8. In addition, changes in transmembrane pressure difference (kPa) are shown in FIG. 9.

Compared with Comparative Example 3 and Example 5, a rise of the L-lysine production rate is improved further and in addition, the L-lysine production rate and the yield relative to glucose consumption are improved. Moreover, an increasing rate of the transmembrane pressure difference is made smaller than that of Comparative Example 3 so that the transmembrane pressure difference changes at low levels. Appearance of a membrane cleaning effect has therefore been confirmed.

Example 7

Under conditions similar to those employed in Comparative Example 3 except for the following conditions, continuous fermentation was conducted:

Amount of gas supplied from module scrubbing gas supply apparatus (16): none Amount of gas supplied from pipe scrubbing gas supply apparatus (18): none Amount of gas supplied from upstream-of-pump pipe scrubbing gas supply apparatus (20): 1200 ml/min Gas linear velocity: 41.7 cm/s Amount of gas supplied from fermentor gas supply apparatus (21): 75 ml/min.

Changes in microorganism concentration (–) in the fermentation liquid in this Example are shown in FIG. 6; changes in L-lysine production rate (g/L/h) are shown in FIG. 7; and changes in yield (%) relative to glucose consumption are shown in FIG. 8. In addition, changes in transmembrane pressure difference (kPa) are shown in FIG. 9.

Compared with Comparative Example 3, Example 5, and Example 6, a rise of the L-lysine production rate is improved further and in addition, the L-lysine production rate and the yield relative to glucose consumption are improved. Moreover, an increasing rate of the transmembrane pressure difference is made smaller than that of Comparative Example 3 so that the transmembrane pressure difference changes at low levels. Appearance of a membrane cleaning effect has therefore been confirmed. It has therefore been confirmed that scrubbing shows its effect irrespective of its supplying position.

Example 8

Under conditions similar to those employed in Comparative Example 3 except for the following conditions, continuous fermentation was conducted:

Amount of gas supplied from module scrubbing gas supply apparatus (16): none Amount of gas supplied from pipe scrubbing gas supply apparatus (18): none Amount of gas supplied from upstream-of-pump pipe scrubbing gas supply apparatus (20): 1500 ml/min Gas linear velocity: 52.1 cm/s Amount of gas supplied from fermentor gas supply apparatus (21): 75 ml/min.

Changes in microorganism concentration (–) in the fermentation liquid in this Example are shown in FIG. 6; changes in L-lysine production rate (g/L/h) are shown in FIG. 7; and changes in yield (%) relative to glucose consumption are shown in FIG. 8. In addition, changes in transmembrane pressure difference (kPa) are shown in FIG. 9.

Compared with Comparative Example 3, a rise of the L-lysine production rate is improved further and in addition, the L-lysine production rate and the yield relative to glucose consumption at the initial stage of operation are improved. Moreover, an increasing rate of the transmembrane pressure difference is made smaller than that of Comparative Example 3 so that the transmembrane pressure difference changes at low levels. Appearance of a membrane cleaning effect has therefore been confirmed. It has been confirmed from the comparison with Comparative Example 4 that long-term operation can be conducted in the present example because of less foaming and a normally controlled liquid surface level.

J. Production of L-Lactic Acid Through Continuous Fermentation

Comparative Example 5

By using the continuous fermentation apparatus shown in FIG. 1, continuous fermentation of L-lactic acid was conducted. As the separation membrane, the hollow fiber membrane manufactured in [F] was used. The following are common operation conditions in continuous fermentation of L-lactic acid.

Common Conditions:
  Microorganism: *Saccharomyces cerevisiae* SU014 strain
  Medium: fermentation medium (Table 3)
  Volume of fermentation liquid: 1.0 (L)
  Hollow fiber membrane MD volume: 0.007 (L)
  Temperature: 32 (° C.)
  Fermentor stirring rate: 400 (rpm)
  Sterilization: a fermentor including a hollow fiber membrane module and a medium used are all subjected to high-pressure (2 atmospheric pressures) steam sterilization in an autoclave at 121° C. for 20 min.
  pH Adjustment: adjusted to pH 4.5 with a 5N aqueous solution of calcium hydroxide
  Circulating pump flow rate: 1.7 L/min
  Filtration rate: 225 ml/h (fixed)

TABLE 3

Yeast lactic acid fermentation medium

| Raw material sugar | 100 | g |
|---|---|---|
| Ammonium sulfate | 1.5 | g |
| up to 1 L | | |

Altered Conditions:
  Amount of gas supplied from module scrubbing gas supply apparatus (16): none
  Amount of gas supplied from pipe scrubbing gas supply apparatus (18): 1 mL/min
  Amount of gas supplied from upstream-of-pump pipe scrubbing gas supply apparatus (20): none
  Gas linear velocity: 0.035 cm/s
  Amount of gas supplied from fermentor gas supply apparatus (21): 125 ml/min A SW-1 strain scraped off from an agar medium was inoculated in a test tube charged with 5 ml of an SC medium (glucose: 100 g/L, yeast nitrogen base: 6.7 g/L, standard 19 amino acids except leucine: 152 mg/L, leucine: 760 mg/L, inositol: 152 mg/L, p-aminobenzoic acid: 16 mg/L, adenine: 40 mg/L, and uracil: 152 mg/L), followed by shaking culture at 30° C. for 24 hours (pre-preculture). All the amount of the pre-preculture medium thus obtained was inoculated in a 500-mL conical flask charged with 50 mL of the medium shown in Table 3 and precultured at 30° C. The preculture medium thus obtained was inoculated in a continuous fermentation apparatus charged with 1.0 L of an L-lactic acid fermentation medium and cultured for 24 hours. Then, continuous culturing was conducted by continuously supplying an L-lactic acid fermentation medium while controlling the supply amount of the culture medium in the fermentor to be constant. In such a manner, production of L-lactic acid through continuous fermentation was conducted.

The concentration of L-lactic acid produced in the filtrate and the residual glucose concentration were measured as needed according the methods shown in [C] and [D], respectively.

Figure 10:
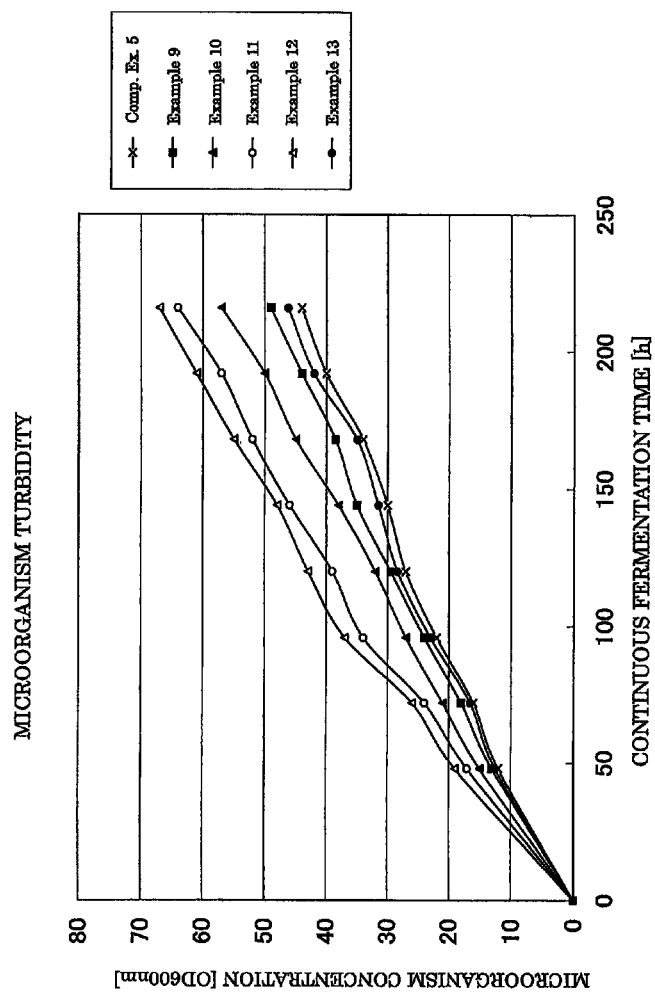
FIG. 10 is a chart showing a change in microorganism concentration in Comparative Example 5 and Examples 9 to 13.
Figure 11:
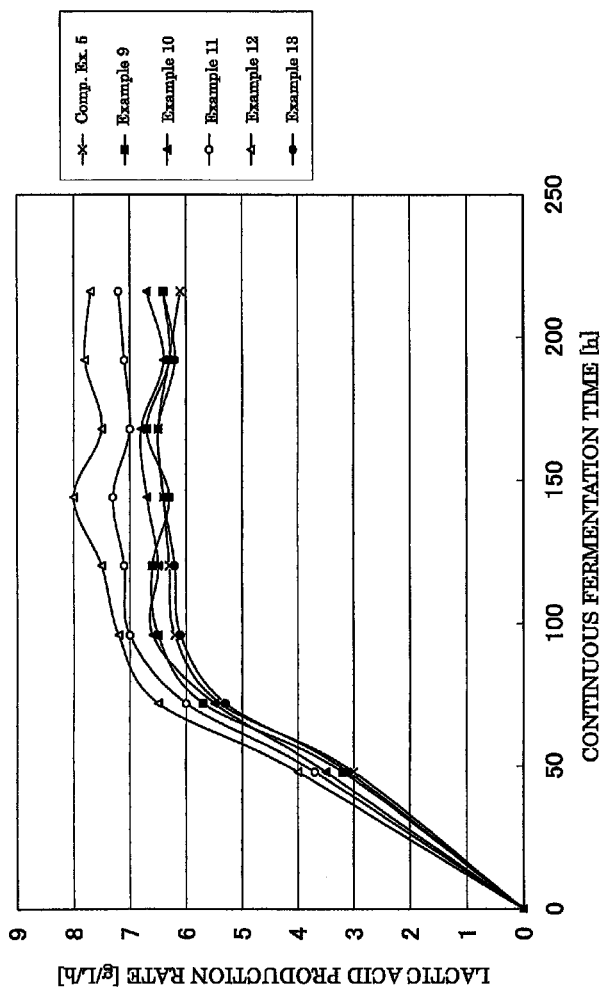
FIG. 11 is a chart showing a change in production rate in Comparative Example 5 and Examples 9 to 13.
Figure 12:
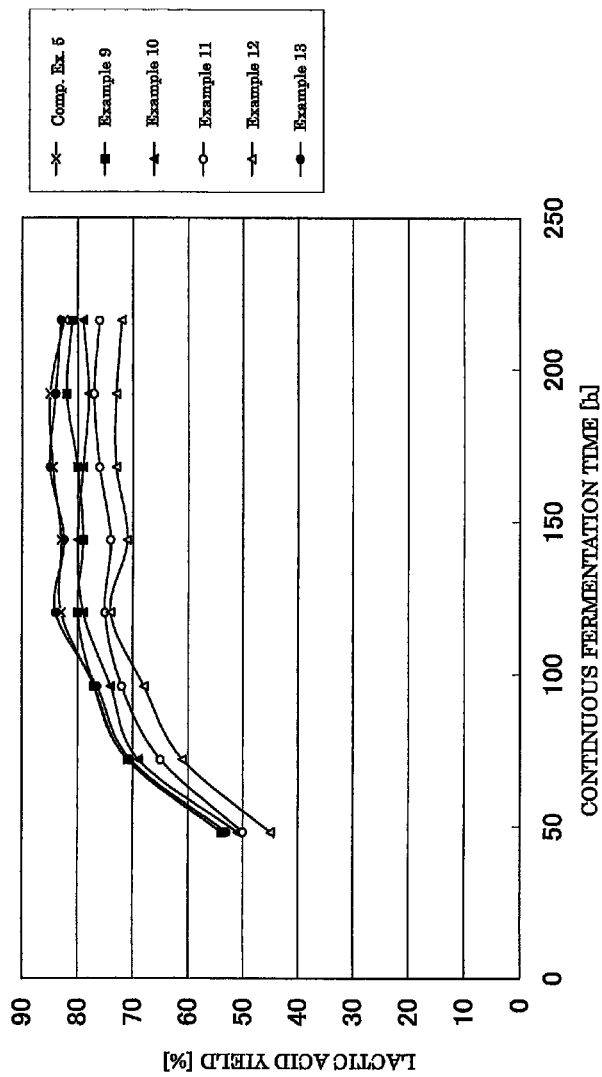
FIG. 12 is a chart showing a change in yield relative to glucose consumption in Comparative Example 5 and Examples 9 to 13.
Figure 13:
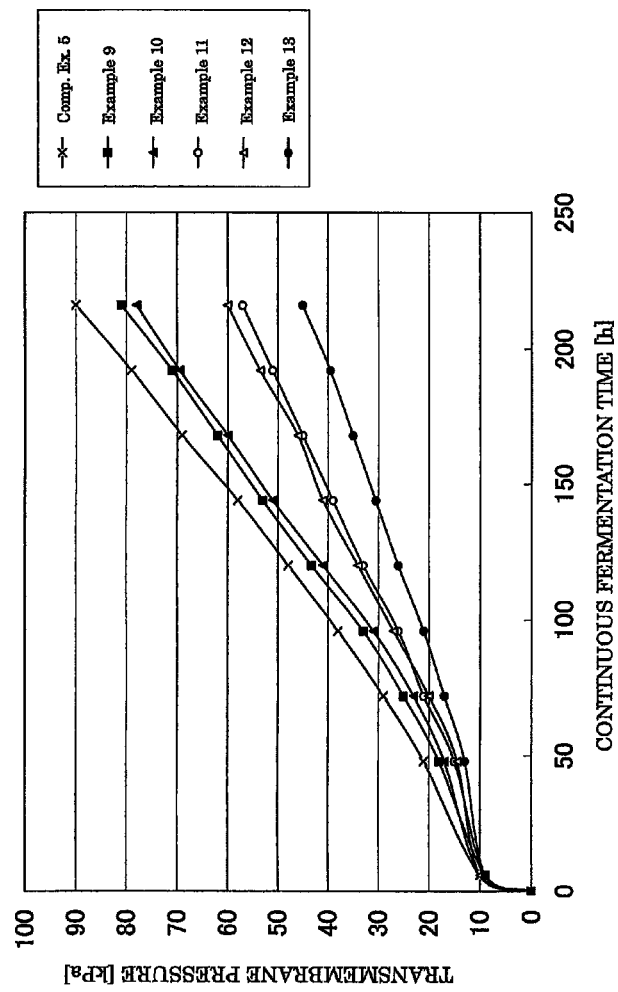
FIG. 13 is a chart showing a change in transmembrane pressure difference in Comparative Example 5 and Examples 9 to 13.

Changes in microorganism concentration (–) in the fermentation liquid in the present Comparative Example are shown in FIG. 10; changes in L-lactic acid production rate (g/L/h) are shown in FIG. 11; and changes in yield (%) relative to glucose consumption are shown in FIG. 12. In addition, changes in transmembrane pressure difference (kPa) are shown in FIG. 13.

Example 9

Under conditions similar to those employed in Comparative Example 5 except for the following conditions, continuous fermentation was conducted:
  Amount of gas supplied from module scrubbing gas supply apparatus (16): none
  Amount of gas supplied from pipe scrubbing gas supply apparatus (18): 4 ml/min
  Amount of gas supplied from upstream-of-pump pipe scrubbing gas supply apparatus (20): none
  Gas linear velocity: 0.15 cm/s
  Amount of gas supplied from fermentor gas supply apparatus (21): 125 ml/min.

Changes in microorganism concentration (–) in the fermentation liquid in this Example are shown in FIG. 10; changes in L-lactic acid production rate (g/L/h) are shown in FIG. 11; and changes in yield (%) relative to glucose consumption are shown in FIG. 12. In addition, changes in transmembrane pressure difference (kPa) are shown in FIG. 13.

Compared with Comparative Example 5, the yield relative to glucose consumption shows a slight decrease but the production rate of L-lactic acid is improved. An increasing rate of the transmembrane pressure difference is made smaller than that of Comparative Example 5 so that the transmembrane pressure difference changes at low levels. Appearance of a membrane cleaning effect has therefore been confirmed. It has been confirmed from comparison with Comparative Example 6 that long-term operation can be conducted in the present example because of less foaming and a normally controlled liquid surface level.

Example 10

Under conditions similar to those employed in Comparative Example 5 except for the following conditions, continuous fermentation was conducted:
  Amount of gas supplied from module scrubbing gas supply apparatus (16): none
  Amount of gas supplied from pipe scrubbing gas supply apparatus (18): 5 ml/min
  Amount of gas supplied from upstream-of-pump pipe scrubbing gas supply apparatus (20): none
  Gas linear velocity: 0.18 cm/s
  Amount of gas supplied from fermentor gas supply apparatus (21): 150 ml/min.

Changes in microorganism concentration (–) in the fermentation liquid in this Example are shown in FIG. 10; changes in L-lactic acid production rate (g/L/h) are shown in FIG. 11; and changes in yield (%) relative to glucose consumption are shown in FIG. 12. In addition, changes in transmembrane pressure difference (kPa) are shown in FIG. 13.

Compared with Comparative Example 5, the yield relative to glucose consumption shows a slight decrease but the L-lactic acid production rate is improved. An increasing rate of the transmembrane pressure difference is made smaller than that of Comparative Example 5 so that the transmembrane pressure difference changes at low levels. Appearance of a membrane cleaning effect has therefore been confirmed. It has been confirmed from comparison with Comparative Example 6 that long-term operation can be conducted because of less foaming and a normally controlled liquid surface level.

Example 11

Under conditions similar to those employed in Comparative Example 5 except for the following conditions, continuous fermentation was conducted:
Amount of gas supplied from module scrubbing gas supply apparatus (16): none
Amount of gas supplied from pipe scrubbing gas supply apparatus (18): 10 ml/min
Amount of gas supplied from upstream-of-pump pipe scrubbing gas supply apparatus (20): none
Gas linear velocity: 0.35 cm/s
Amount of gas supplied from fermentor gas supply apparatus (21): 125 ml/min.

Changes in microorganism concentration (–) in the fermentation liquid in this Example are shown in FIG. 10; changes in L-lactic acid production rate (g/L/h) are shown in FIG. 11; and changes in yield (%) relative to glucose consumption are shown in FIG. 12. In addition, changes in transmembrane pressure difference (kPa) are shown in FIG. 13.

Compared with Comparative Example 5, the yield relative to glucose consumption shows a slight decrease but the L-lactic acid production rate is improved. An increasing rate of the transmembrane pressure difference is made smaller than that of Comparative Example 5 so that the transmembrane pressure difference changes at low levels. Appearance of a membrane cleaning effect has therefore been confirmed. It has been confirmed from comparison with Comparative Example 6 that long-term operation can be conducted because of less foaming and a normally controlled liquid surface level.

Example 12

Under conditions similar to those employed in Comparative Example 5 except for the following conditions, continuous fermentation was conducted:
Amount of gas supplied from module scrubbing gas supply apparatus (16): none
Amount of gas supplied from pipe scrubbing gas supply apparatus (18): none
Amount of gas supplied from upstream-of-pump pipe scrubbing gas supply apparatus (20): 10 ml/min
Gas linear velocity: 0.35 cm/s
Amount of gas supplied from fermentor gas supply apparatus (21): 125 ml/min.

Changes in microorganism concentration (–) in the fermentation liquid in this Example are shown in FIG. 10; changes in L-lactic acid production rate (g/L/h) are shown in FIG. 11; and changes in yield (%) relative to glucose consumption are shown in FIG. 12. In addition, changes in transmembrane pressure difference (kPa) are shown in FIG. 13.

Compared with Comparative Example 5, the yield relative to glucose consumption shows a slight decrease but the L-lactic acid production rate is improved. An increasing rate of the transmembrane pressure difference is made smaller than that of Comparative Example 5 so that the transmembrane pressure difference changes at low levels. Appearance of a membrane cleaning effect has therefore been confirmed. It has been confirmed from comparison with Comparative Example 6 that long-term operation can be conducted because of less foaming and a normally controlled liquid surface level. Compared with Example 11, supply of a gas from the upstream-pump pipe distant from the module slightly increased a lactic acid production rate even at the same gas linear velocity.

Example 13

Under conditions similar to those employed in Comparative Example 5 except for the following conditions, continuous fermentation was conducted:
Amount of gas supplied from module scrubbing gas supply apparatus (16): none
Amount of gas supplied from pipe scrubbing gas supply apparatus (18): 20 ml/min
Amount of gas supplied from upstream-of-pump pipe scrubbing gas supply apparatus (20): none
Gas linear velocity: 0.71 cm/s
Amount of gas supplied from fermentor gas supply apparatus (21): 0 ml/min.

Changes in microorganism concentration (–) in the fermentation liquid in this Example are shown in FIG. 10; changes in L-lactic acid production rate (g/L/h) are shown in FIG. 11; and changes in yield (%) relative to glucose concentration are shown in FIG. 12. In addition, changes in transmembrane pressure difference (kPa) are shown in FIG. 13.

The L-lactic acid production rate and the yield relative to glucose consumption are equal to those of Comparative Example 5 in which the fermentor had been aerated at 125 min/mL. Moreover, an increasing rate of the transmembrane pressure difference is made smaller than that of Comparative Example 5 so that the transmembrane pressure difference changes at low levels. Appearance of a membrane cleaning effect has therefore been confirmed. Aeration from the bottom of MD considerably reduces the aeration amount and thereby reduces an operation cost and produces a cleaning effect of the membrane. As a result, stable continuous fermentation can be conducted for a long period of time. It has also been confirmed that compared with Comparative Example 6, operation can be conducted for a long period of time because of less foaming and a normally controlled liquid surface level.

Comparative Example 6

Under conditions similar to those employed in Comparative Example 5 except for the following conditions, continuous fermentation was conducted:
Amount of gas supplied from module scrubbing gas supply apparatus (16): none
Amount of gas supplied from pipe scrubbing gas supply apparatus (18): none
Amount of gas supplied from upstream-of-pump pipe scrubbing gas supply apparatus (20): 2300 ml/min
Gas linear velocity: 81.3 cm/s
Amount of gas supplied from fermentor gas supply apparatus (21): 0 ml/min.

In this Comparative Example, foams generated severely in the fermentor reached the exhaust port present in the upper portion of the fermentor and come into contact with the outside air and therefore, contamination occurred, making it impossible to conduct continuous fermentation.

INDUSTRIAL APPLICABILITY

In our methods, since a simple and easy method of supplying a separation membrane module with a gas is employed, it is possible to improve the long-term stability of separation membrane module operation and fermentation results while suppressing the possibility of causing contamination with unwanted microorganisms other than microorganisms necessary for culture. This method is therefore used widely in the fermentation industry and contributes to stable production of a chemical, which is a fermentation product, at a low cost.

The invention claimed is:

1. A method of producing a chemical through continuous fermentation comprising:

(a) culturing a cell in a culture medium in a fermentor to ferment a feedstock to produce a chemical;

(b) conducting filtration of the culture medium with a separation membrane module;

(c) separating a permeate containing the chemical from the culture medium while retaining a non-permeated liquid in the fermentor, and (d) supplying a gas from at least one of a lower portion of the separation membrane module and a pipe communicating between the fermentor and the separation membrane module to adjust a gas linear velocity in the separation membrane module to 0.15 cm/s to 70 cm/s while supplying the separation membrane module with the culture medium.

2. The method according to claim 1, wherein in (d), the gas contains oxygen.

3. The method according to claim 2, further comprising, in addition to (d), (e) supplying the fermentor with a gas, wherein:
the gas is supplied in (d) intermittently, and
when the gas is not supplied in (d), a supply rate of the gas in (e) is increased compared with that when the gas is supplied in (d).

4. The method according to claim 1, wherein the filtration in (b) is conducted intermittently.

5. The method according to claim 1, wherein the cell is a microorganism.

6. The method according to claim 5, wherein the microorganism is a microorganism belonging to any of the Genus *Escherichia*, the Genus *Providencia*, the Genus *Corynebacterium*, the Genus *Brevibacterium*, and the Genus *Serratia*.

7. The method according to claim 6, wherein the microorganism is any of *Escherichia coli, Providencia rettgeri, Corynebacterium glutamicum, Brevibacterium flavum, Brevibacterium lactofermentum*, and *Serratia marcescens*.

8. The method according to claim 1, wherein the cell is a yeast.

9. The method according to claim 1, wherein the chemical is an amino acid.

10. The method according to claim 9, wherein the amino acid is L-threonine, L-lysine, L-glutamic acid, L-tryptophan, L-isoleucine, L-glutamine, L-arginine, L-alanine, L-histidine, L-proline, L-phenylalanine, L-aspartic acid, L-tyrosine, L-methionine, L-serine, L-valine, or L-leucine.

11. The method according to claim 1, wherein the chemical is an organic acid.

12. The method according to claim 11, wherein the chemical is lactic acid.

13. The method according to claim 1, wherein the chemical is cadaverine.

\* \* \* \* \*